(12) United States Patent
Kinast et al.

(10) Patent No.: US 11,234,602 B2
(45) Date of Patent: *Feb. 1, 2022

(54) NON-INVASIVE BLOOD PRESSURE MEASUREMENT SYSTEM

(71) Applicant: Masimo Corporation, Irvine, CA (US)

(72) Inventors: Eric Karl Kinast, Santa Ana, CA (US); Valery G. Telfort, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 283 days.

This patent is subject to a terminal disclaimer.

(21) Appl. No.: 16/047,684

(22) Filed: Jul. 27, 2018

(65) Prior Publication Data

US 2019/0090760 A1 Mar. 28, 2019

Related U.S. Application Data

(63) Continuation of application No. 15/229,840, filed on Aug. 5, 2016, now Pat. No. 10,052,037, which is a
(Continued)

(51) Int. Cl.
*A61B 5/021* (2006.01)
*A61B 7/00* (2006.01)
(Continued)

(52) U.S. Cl.
CPC ........ *A61B 5/02125* (2013.01); *A61B 5/0205* (2013.01); *A61B 5/02028* (2013.01); *A61B 5/0261* (2013.01); *A61B 5/0285* (2013.01); *A61B 5/0295* (2013.01); *A61B 5/02255* (2013.01); *A61B 5/02405* (2013.01); *A61B 5/02416* (2013.01); *A61B 5/318* (2021.01); *A61B 5/7203* (2013.01); *A61B 5/725* (2013.01); *A61B 5/7246* (2013.01); *A61B 5/7271* (2013.01); *A61B 7/00* (2013.01); *A61B 7/02* (2013.01); *A61B 7/045* (2013.01);
(Continued)

(58) Field of Classification Search
CPC .................................................. A61B 5/02125
See application file for complete search history.

(56) References Cited

U.S. PATENT DOCUMENTS 4,960,128 A 10/1990 Gordon et al.
4,964,408 A 10/1990 Hink et al.
(Continued)

*Primary Examiner* — Meredith Weare
(74) *Attorney, Agent, or Firm* — Knobbe Martens Olson & Bear, LLP

(57) ABSTRACT

A system for non-invasively determining an indication of an individual's blood pressure is described. In certain embodiments, the system calculates pulse wave transit time using two acoustic sensors. The system can include a first acoustic sensor configured to monitor heart sounds of the patient corresponding to ventricular systole and diastole and a second acoustic sensor configured to monitor arterial pulse sounds at an arterial location remote from the heart. The system can advantageously calculate a arterial pulse wave transit time (PWTT) that does not include the pre-ejection period time delay. In certain embodiments, the system further includes a processor that calculates the arterial PWTT obtained from the acoustic sensors. The system can use this arterial PWTT to determine whether to trigger an occlusive cuff measurement.

14 Claims, 25 Drawing Sheets

Related U.S. Application Data continuation of application No. 13/189,396, filed on Jul. 22, 2011, now Pat. No. 9,408,542.

(60) Provisional application No. 61/469,511, filed on Mar. 30, 2011, provisional application No. 61/366,862, filed on Jul. 22, 2010.

(51) Int. Cl.

| | | |
|---|---|---|
| *A61B 5/024* | (2006.01) | |
| *A61B 5/00* | (2006.01) | |
| *A61B 5/026* | (2006.01) | |
| *A61B 5/0285* | (2006.01) | |
| *A61B 5/0295* | (2006.01) | |
| *A61B 7/04* | (2006.01) | |
| *A61B 5/318* | (2021.01) | |
| *A61B 5/02* | (2006.01) | |
| *A61B 5/0205* | (2006.01) | |
| *A61B 5/0225* | (2006.01) | |
| *A61B 7/02* | (2006.01) | |
| *A61B 8/02* | (2006.01) | |
| *A61B 5/029* | (2006.01) | |
| *A61B 5/053* | (2021.01) | |
| *A61B 5/349* | (2021.01) | |
| *A61B 5/0245* | (2006.01) | |
| *A61B 5/08* | (2006.01) | |
| *A61B 5/1455* | (2006.01) | |

(52) U.S. Cl.
CPC ............... *A61B 8/02* (2013.01); *A61B 5/024* (2013.01); *A61B 5/029* (2013.01); *A61B 5/0245* (2013.01); *A61B 5/053* (2013.01); *A61B 5/0816* (2013.01); *A61B 5/14551* (2013.01); *A61B 5/349* (2021.01); *A61B 2560/0223* (2013.01); *A61B 2562/0204* (2013.01); *A61B 2562/04* (2013.01); *A61B 2562/06* (2013.01)

(56) References Cited

U.S. PATENT DOCUMENTS

| | | | |
|---|---|---|---|
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,685,299 | A | 11/1997 | Diab et al. |
| D393,830 | S | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |

(56) References Cited

U.S. PATENT DOCUMENTS

| | | |
|---|---|---|
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,519,327 B2 | 4/2009 | White |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,601,123 B2 | 10/2009 | Tweed et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,726,209 B2 | 6/2010 | Ruotoistenmaki |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |

(56) References Cited

U.S. PATENT DOCUMENTS

| | | |
|---|---|---|
| 7,844,313 B2 | 11/2010 | Kiani et al. |
| 7,844,314 B2 | 11/2010 | Al-Ali |
| 7,844,315 B2 | 11/2010 | Al-Ali |
| 7,862,523 B2 | 1/2011 | Ruotoistenmaki |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,289,130 B2 | 10/2012 | Nakajima et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,364,389 B2 | 1/2013 | Dorogusker et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,615,290 B2 | 12/2013 | Lin et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,655,004 B2 | 2/2014 | Prest et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |

(56) References Cited

U.S. PATENT DOCUMENTS

| | | |
|---|---|---|
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,760,517 B2 | 6/2014 | Sarwar et al. |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Ai-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Ai-Ali et al. |
| 8,920,317 B2 | 12/2014 | Ai-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,437 B2 | 7/2015 | Paalasmaa |
| 9,072,474 B2 | 7/2015 | Al-Ali et al. |
| 9,078,560 B2 | 7/2015 | Schurman et al. |
| 9,081,889 B2 | 7/2015 | Ingrassia, Jr. et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,210,566 B2 | 12/2015 | Ziemianska et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,311,382 B2 | 4/2016 | Varoglu et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,357,665 B2 | 5/2016 | Myers et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,489,081 B2 | 11/2016 | Anzures et al. |
| 9,492,110 B2 | 11/2016 | Al-Ali et al. |
| 9,497,534 B2 | 11/2016 | Prest et al. |
| 9,510,779 B2 | 12/2016 | Poeze et al. |
| 9,517,024 B2 | 12/2016 | Kiani et al. |
| 9,526,430 B2 | 12/2016 | Srinivas et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,553,625 B2 | 1/2017 | Hatanaka et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,593,969 B2 | 3/2017 | King |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |

(56) References Cited

U.S. PATENT DOCUMENTS

| | | |
|---|---|---|
| 9,636,056 B2 | 5/2017 | Al-Ali |
| 9,649,054 B2 | 5/2017 | Lamego et al. |
| 9,651,405 B1 | 5/2017 | Gowreesunker et al. |
| 9,662,052 B2 | 5/2017 | Al-Ali et al. |
| 9,668,676 B2 | 6/2017 | Culbert |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,699,546 B2 | 7/2017 | Qian et al. |
| 9,716,937 B2 | 7/2017 | Qian et al. |
| 9,717,425 B2 | 8/2017 | Kiani et al. |
| 9,717,458 B2 | 8/2017 | Lamego et al. |
| 9,723,997 B1 | 8/2017 | Lamego |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Ai-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,781,984 B2 | 10/2017 | Baranski et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,838,775 B2 | 12/2017 | Qian et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,848,823 B2 | 12/2017 | Raghuram et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,866,671 B1 | 1/2018 | Thompson et al. |
| 9,867,575 B2 | 1/2018 | Maani et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,898,049 B2 | 2/2018 | Myers et al. |
| 9,913,617 B2 | 3/2018 | Al-Ali et al. |
| 9,918,646 B2 | 3/2018 | Singh Alvarado et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,952,095 B1 | 4/2018 | Hotelling et al. |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,080 B2 | 7/2018 | Miller et al. |
| 10,039,482 B2 | 8/2018 | Al-Ali et al. |
| 10,052,037 B2 * | 8/2018 | Kinast .................. A61B 5/0402 |
| 10,055,121 B2 | 8/2018 | Chaudhri et al. |
| 10,058,275 B2 | 8/2018 | Al-Ali et al. |
| 10,064,562 B2 | 9/2018 | Al-Ali |
| 10,066,970 B2 | 9/2018 | Gowreesunker et al. |
| 10,076,257 B2 | 9/2018 | Lin et al. |
| 10,078,052 B2 | 9/2018 | Ness et al. |
| 2002/0001390 A1 * | 1/2002 | Kawaguchi .............. A61B 7/00 381/67 |
| 2003/0220577 A1 * | 11/2003 | Bartels ............... A61B 5/02125 600/510 |
| 2004/0030261 A1 * | 2/2004 | Rantala ............. A61B 5/02125 600/561 |
| 2004/0267148 A1 * | 12/2004 | Arand ................. A61B 5/0456 600/528 |
| 2006/0047213 A1 * | 3/2006 | Gavriely ............ A61B 5/02405 600/513 |
| 2006/0161054 A1 | 7/2006 | Reuss et al. |
| 2007/0282478 A1 | 12/2007 | Al-Ali et al. |
| 2008/0243202 A1 * | 10/2008 | Patangay ................. A61B 7/00 607/27 |
| 2009/0227879 A1 * | 9/2009 | Matsumoto ........ A61B 5/02438 600/501 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0317933 A1 * | 12/2010 | Colman ............... A61B 5/0205 600/301 |
| 2010/0331708 A1 * | 12/2010 | Hatib ...................... A61B 5/02 600/481 |
| 2011/0066010 A1 * | 3/2011 | Moon ................... A61B 5/742 600/301 |
| 2011/0082711 A1 | 4/2011 | Poeze et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |

(56) References Cited

U.S. PATENT DOCUMENTS

| | | |
|---|---|---|
| 2014/0171146 A1 | 6/2014 | Ma et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0173671 A1 | 6/2015 | Paalasmaa et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0255001 A1 | 9/2015 | Haughay et al. |
| 2015/0257689 A1 | 9/2015 | Al-Ali et al. |
| 2015/0272514 A1 | 10/2015 | Kiani et al. |
| 2015/0281424 A1 | 10/2015 | Vock et al. |
| 2015/0318100 A1 | 11/2015 | Rothkopf et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0019360 A1 | 1/2016 | Pahwa et al. |
| 2016/0023245 A1 | 1/2016 | Zadesky et al. |
| 2016/0029932 A1 | 2/2016 | Al-Ali |
| 2016/0038045 A1 | 2/2016 | Shapiro |
| 2016/0051157 A1 | 2/2016 | Waydo |
| 2016/0051158 A1 | 2/2016 | Silva |
| 2016/0058302 A1 | 3/2016 | Raghuram et al. |
| 2016/0058309 A1 | 3/2016 | Han |
| 2016/0058312 A1 | 3/2016 | Han et al. |
| 2016/0058347 A1 | 3/2016 | Reichgott et al. |
| 2016/0058356 A1 | 3/2016 | Raghuram et al. |
| 2016/0058370 A1 | 3/2016 | Raghuram et al. |
| 2016/0066824 A1 | 3/2016 | Al-Ali et al. |
| 2016/0071392 A1 | 3/2016 | Hankey et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0154950 A1 | 6/2016 | Nakajima et al. |
| 2016/0157780 A1 | 6/2016 | Rimminen et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0213309 A1 | 7/2016 | Sannholm et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0256058 A1 | 9/2016 | Pham et al. |
| 2016/0256082 A1 | 9/2016 | Ely et al. |
| 2016/0267238 A1 | 9/2016 | Nag |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287181 A1 | 10/2016 | Han et al. |
| 2016/0287786 A1 | 10/2016 | Kiani |
| 2016/0296169 A1 | 10/2016 | McHale et al. |
| 2016/0296173 A1 | 10/2016 | Culbert |
| 2016/0296174 A1 | 10/2016 | Isikman et al. |
| 2016/0310027 A1 | 10/2016 | Han |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2016/0378069 A1 | 12/2016 | Rothkopf |
| 2016/0378071 A1 | 12/2016 | Rothkopf |
| 2017/0000394 A1 | 1/2017 | Al-Ali et al. |
| 2017/0007134 A1 | 1/2017 | Al-Ali et al. |
| 2017/0007183 A1 | 1/2017 | Dusan et al. |
| 2017/0007198 A1 | 1/2017 | Al-Ali et al. |
| 2017/0010858 A1 | 1/2017 | Prest et al. |
| 2017/0014083 A1 | 1/2017 | Diab et al. |
| 2017/0014084 A1 | 1/2017 | Al-Ali et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0074897 A1 | 3/2017 | Mermel et al. |
| 2017/0079594 A1 | 3/2017 | Telfort et al. |
| 2017/0084133 A1 | 3/2017 | Cardinali et al. |
| 2017/0086689 A1 | 3/2017 | Shui et al. |
| 2017/0086723 A1 | 3/2017 | Al-Ali et al. |
| 2017/0086742 A1 | 3/2017 | Harrison-Noonan et al. |
| 2017/0086743 A1 | 3/2017 | Bushnell et al. |
| 2017/0094450 A1 | 3/2017 | Tu et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0164884 A1 | 6/2017 | Culbert et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0248446 A1 | 8/2017 | Gowreesunker et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0273619 A1 | 9/2017 | Alvarado et al. |
| 2017/0281024 A1 | 10/2017 | Narasimhan et al. |
| 2017/0293727 A1 | 10/2017 | Klaassen et al. |
| 2017/0311851 A1 | 11/2017 | Schurman et al. |
| 2017/0311891 A1 | 11/2017 | Kiani et al. |
| 2017/0325698 A1 | 11/2017 | Allec et al. |
| 2017/0325728 A1 | 11/2017 | Al-Ali et al. |
| 2017/0325744 A1 | 11/2017 | Allec et al. |
| 2017/0332976 A1 | 11/2017 | Al-Ali et al. |
| 2017/0340209 A1 | 11/2017 | Klaassen et al. |
| 2017/0340219 A1 | 11/2017 | Sullivan et al. |
| 2017/0340293 A1 | 11/2017 | Al-Ali et al. |
| 2017/0347885 A1 | 12/2017 | Tan et al. |
| 2017/0354332 A1 | 12/2017 | Lamego |
| 2017/0354795 A1 | 12/2017 | Blahnik et al. |
| 2017/0358239 A1 | 12/2017 | Arney et al. |
| 2017/0358240 A1 | 12/2017 | Blahnik et al. |
| 2017/0358242 A1 | 12/2017 | Thompson et al. |
| 2017/0360306 A1 | 12/2017 | Narasimhan et al. |
| 2017/0360310 A1 | 12/2017 | Kiani et al. |
| 2017/0366657 A1 | 12/2017 | Thompson et al. |
| 2017/0367632 A1 | 12/2017 | Al-Ali et al. |
| 2018/0008146 A1 | 1/2018 | Al-Ali et al. |

(56) References Cited

U.S. PATENT DOCUMENTS

| | | |
|---|---|---|
| 2018/0014752 A1 | 1/2018 | Al-Ali et al. |
| 2018/0014781 A1 | 1/2018 | Clavelle et al. |
| 2018/0025287 A1 | 1/2018 | Mathew et al. |
| 2018/0056129 A1 | 1/2018 | Narasimha Rao et al. |
| 2018/0028124 A1 | 2/2018 | Al-Ali et al. |
| 2018/0042556 A1 | 2/2018 | Shahparnia et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0055439 A1 | 3/2018 | Pham et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0078151 A1 | 3/2018 | Allec et al. |
| 2018/0078182 A1 | 3/2018 | Chen et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110469 A1 | 4/2018 | Maani et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153418 A1 | 6/2018 | Sullivan et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0164853 A1 | 6/2018 | Myers et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0196514 A1 | 7/2018 | Allec et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0228414 A1 | 8/2018 | Shao et al. |
| 2018/0238718 A1 | 8/2018 | Dalvi |
| 2018/0238734 A1 | 8/2018 | Hotelling et al. |
| 2018/0242853 A1 | 8/2018 | Al-Ali |
| 2018/0242921 A1 | 8/2018 | Muhsin et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0279956 A1 | 10/2018 | Waydo et al. |

\* cited by examiner

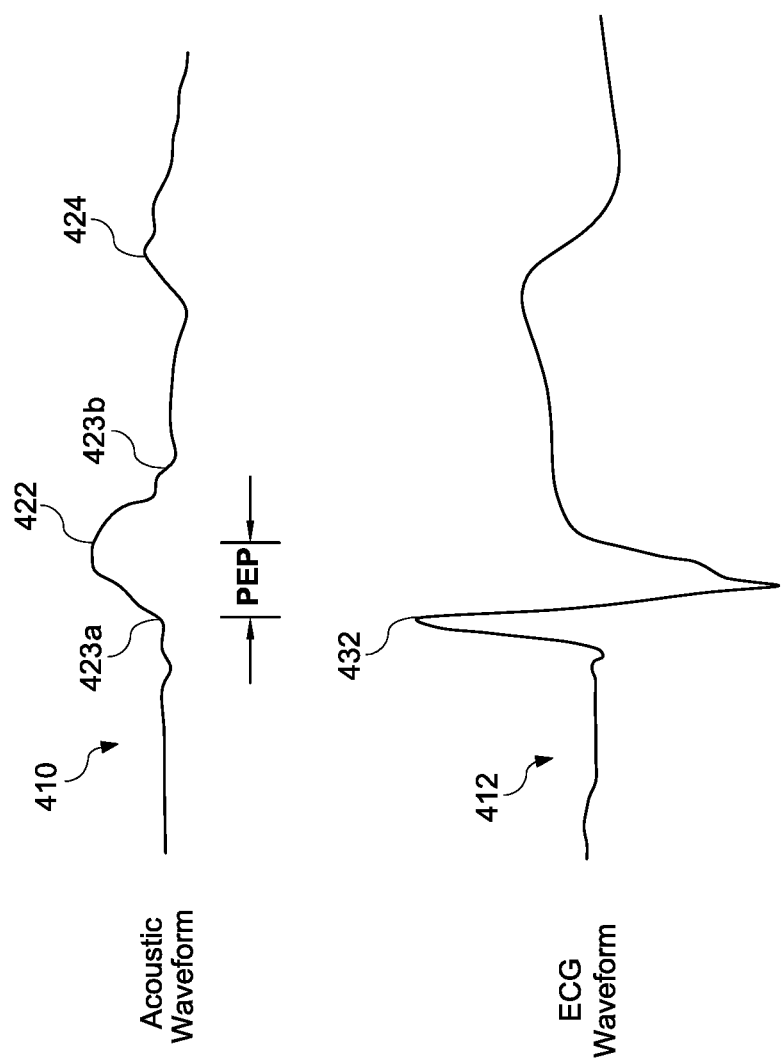

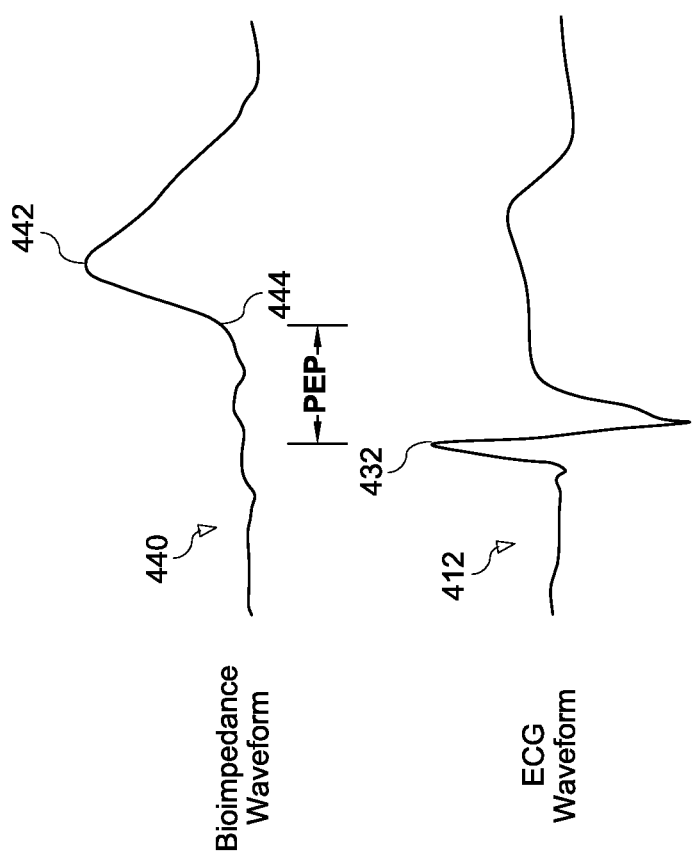

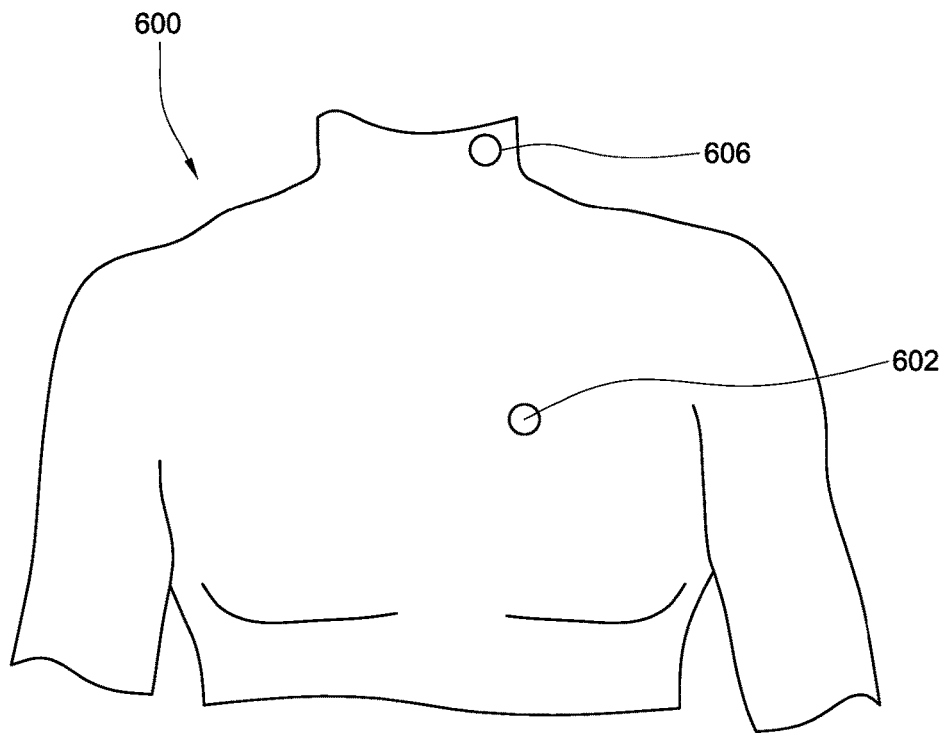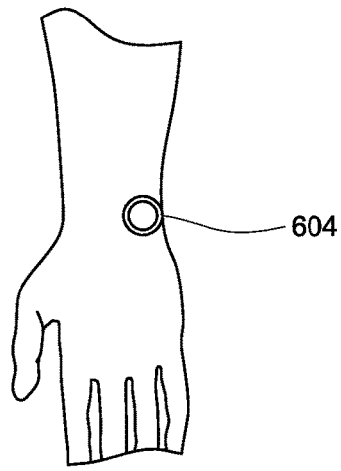
FIG. 6

NON-INVASIVE BLOOD PRESSURE MEASUREMENT SYSTEM

RELATED APPLICATIONS

This application claims priority under 35 U.S.C. § 119(e) to U.S. Provisional Application No. 61/366,862, filed Jul. 22, 2010, entitled "System for Triggering a Non-Invasive Blood Pressure Device" and to U.S. Provisional Application No. 61/469,511, filed Mar. 30, 2011, entitled "Non-Invasive Blood Pressure Measurement System," the disclosures of which are hereby incorporated by reference in their entirety.

BACKGROUND

Prolonged reduction or loss of blood pressure in a patient severely limits the amount of tissue perfusion of the patient and therefore causes damage to or death of the tissue. Although some tissues can tolerate hypoperfusion for long periods of time, the brain, heart and kidneys are very sensitive to a reduction in blood flow. Thus, during and after medical procedures and at other times, blood pressure is a frequently monitored vital sign. Blood pressure can be affected by the type of medical procedure performed and by physiological factors such as the body's reaction to the medical procedure. Moreover, blood pressure is often manipulated and controlled using various medications. Medical procedures, physiological factors, and medications can cause the blood pressure of a patient to change rapidly.

The traditional method of measuring blood pressure is with a stethoscope, occlusive cuff, and pressure manometer. Blood pressure cuff instruments make only a spot-check measurement, so repetitive interval measurements are often used to trend patient status. More frequent intervals improve vigilance at the expense of patient discomfort, possible patient injury (e.g., due to occlusion of blood vessels), and excessive battery consumption.

SUMMARY

In certain embodiments, a method of monitoring blood pressure of a patient includes receiving a physiological electrical signal from an electrical sensor coupled with a patient. The physiological electrical signal can reflect electrical activity of the patient's heart. The method may also include receiving a cardiac ejection signal from a second sensor coupled with the patient. This cardiac ejection signal can reflect a cardiac ejection event associated with ejection of blood from the patient's heart. In addition, the method may include receiving an arterial pulse signal from a third sensor coupled with a limb of the patient. The method can also include determining an arterial pulse wave transit time (PWTT) that compensates for a pre-ejection period of a cardiac cycle associated with the patient's heart, based at least partly on the physiological electrical signal, the cardiac ejection signal, and the arterial pulse signal. Moreover, the method may include triggering an occlusive blood pressure cuff to obtain a blood pressure measurement from the patient responsive to a change in the arterial PWTT.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be reused to indicate correspondence between referenced elements. The drawings are provided to illustrate embodiments of the inventions described herein and not to limit the scope thereof.

FIG. 4A illustrates a plot of acoustic and ECG waveforms;

FIG. 4B illustrates a plot of bioimpedance and ECG waveforms;

FIG. 6 illustrates example positioning locations for the acoustic sensors that can be used in the various systems and methods described herein;

DETAILED DESCRIPTION

Figure 1:
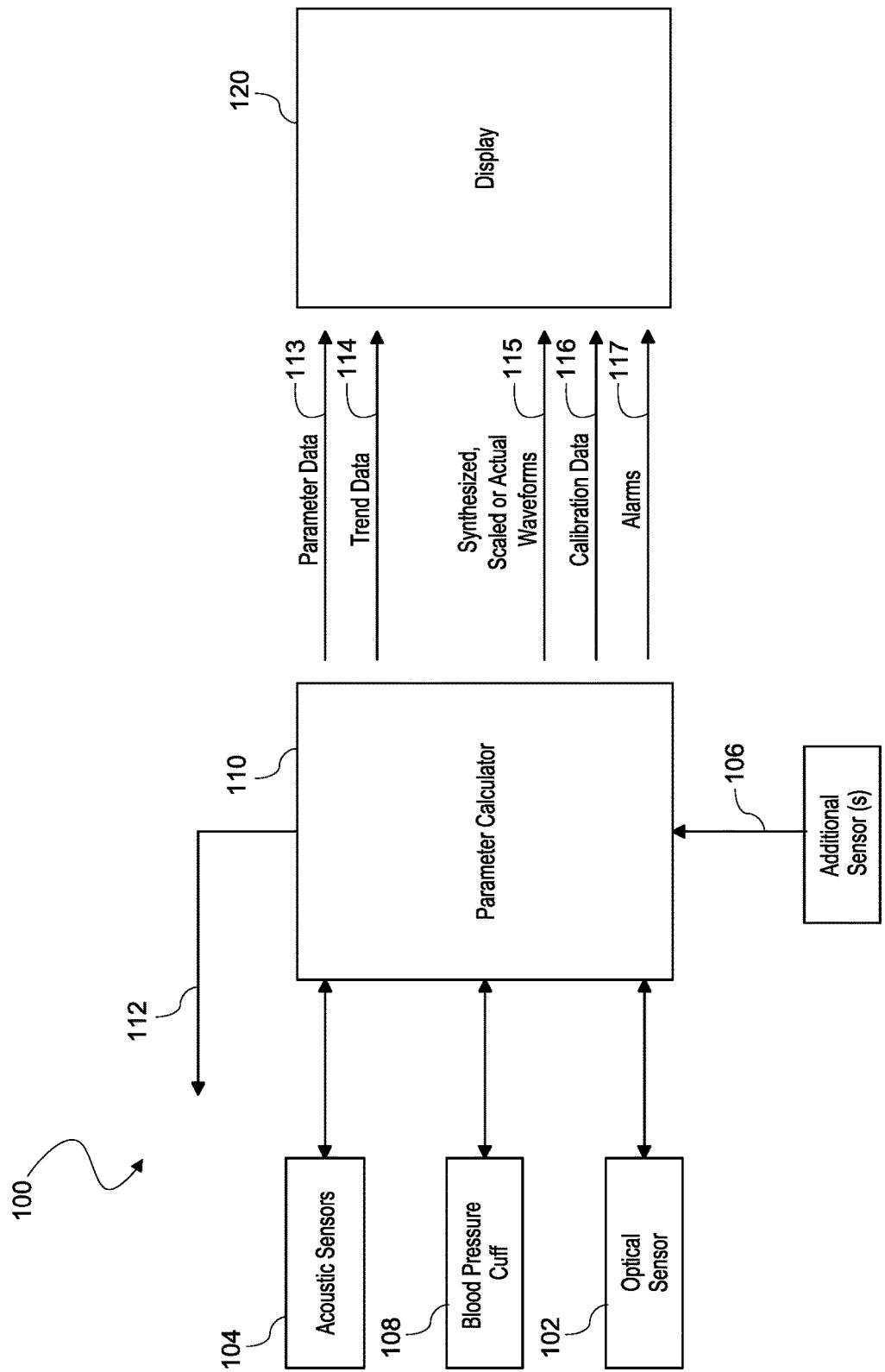
FIG. 1 illustrates an embodiment of a parameter calculation system.

The propagation time of an arterial pulse wave from the heart to an extremity is related to blood pressure. Currently available blood pressure monitoring systems estimate this propagation time by detecting a time difference between points on an electrocardiograph (ECG) waveform and a photoplethysmograph waveform. This estimated propagation time is sometimes referred to as pulse wave transit time (PWTT) or time difference of arrival (TDOA). Currently available blood pressure monitoring systems trigger an automatic occlusive cuff to take a blood pressure measurement based on detected changes in PWTT. When the PWTT has not changed substantially, the blood pressure monitoring system usually does not trigger an occlusive blood pressure measurement. As a result, such a system automatically adjusts the frequency of occlusive blood pressure measurements to obtain better data while potentially reducing discomfort for the patient.

A drawback with existing blood pressure systems is that PWTT as calculated by these systems is not always an accurate indicator of blood pressure or changes in blood pressure. One reason for this inaccuracy is that currently-available systems do not account for a patient's pre-ejection period (PEP) when computing PWTT. The PEP can include the difference in time between an electrical trigger that initiates ventricular contraction (e.g., as detected by an ECG sensor) and the actual ejection of blood from the ventricles into the aorta. Accordingly, the calculated PWTT does not accurately represent the actual propagation time of the arterial pulse from the heart to an extremity, which can result in inaccuracy in the blood pressure variability measurements.

Another reason for the inaccuracy of existing blood pressure systems is that the photoplethysmograph waveform is typically obtained from an optical sensor coupled to a finger of the patient. Studies have shown that pulse wave velocity slows greatly at the transition from the arteries to the smaller vessels and capillaries, adding considerable delay to the arterial PWTT. This time delay can account for up to 50% of the arterial PWTT. The use of an acoustic sensor positioned over an artery to monitor arterial pulse instead of capillary flow can advantageously remove the effect of the artery-to-capillary transition delay component of the arterial pulse wave transit time measurements.

This disclosure describes, among other features, a system for non-invasively determining an indication of an individual's blood pressure. In certain embodiments, the system dynamically accounts for a patient's PEP when calculating PWTT. The system can include an optical sensor that obtains plethysmograph information from a patient. The system can further include an electrical sensor, which can be any sensor that obtains information relating to the electrical activity of the patient's heart (such as an ECG sensor). In addition, the system can include another sensor, such as an acoustic sensor or a bioimpedance sensor, which can obtain information about cardiac ejections from the patient's heart. In certain embodiments, the system further includes a processor that calculates PWTT compensated for PEP using the information obtained from the optical, electrical, acoustic, and/or bioimpedance sensors. The system can use this compensated PWTT to determine whether to trigger an occlusive cuff measurement.

In some embodiments, the system determines an arterial pulse wave transit time measurement from features of two acoustic waveforms. The system can include an acoustic heart sounds sensor that obtains heart sound information from a patient. The system can further include an acoustic pulse sensor, which can be placed at a location remote from the patient's heart at which peripheral arterial pulse pressure wave vibrations can be monitored (such as at a patient's wrist or neck). In addition, the system can include one or more other sensors, such as a second acoustic pulse sensor, ECG sensors, optical sensors, and/or bioimpedance sensors. In certain embodiments, the system further includes a processor that calculates arterial PWTT using the information obtained from the acoustic and/or other sensors. The system can use the arterial PWTT measurements to estimate changes in blood pressure and to aid in determining whether to trigger an occlusive cuff measurement.

In some embodiments, the system also compensates PWTT data for noise. For example, the system can use a noise reference signal to reduce noise in the PWTT data. The noise reference signal can be derived from the patient's heart rate. The system can reduce noise in the PWTT, for example, by adaptively reducing the noise based on the noise reference signal or by dynamically adjusting an averaging time used to average the PWTT data, among other possible techniques.

Moreover, in certain embodiments, the non-invasive blood pressure measurement system also calibrates PWTT data based on an individualized patient calibration factor. A calibration function or curve can be determined that maps PWTT measurements to blood pressure values. The slope of the calibration curve can be determined experimentally and can vary greatly from patient to patient. In some embodiments, the system determines an individualized, or personalized, patient calibration factor based on the determined slope. The patient calibration factor can then be used to interpret subsequent PWTT measurements to estimate changes in blood pressure. The individualized patient calibration can advantageously reduce the occurrence of unnecessary blood pressure cuff measurements and/or false alarms.

System Overview

FIG. 1 illustrates an embodiment of a parameter calculation system 100. In certain embodiments, the parameter calculation system 100 non-invasively obtains an indication of changes in a patient's blood pressure. The parameter calculation system 100 can use the measured blood pressure changes to trigger a blood pressure cuff 108 to obtain an occlusive blood pressure measurement. Advantageously, in certain embodiments, the parameter calculation system 100 uses the arterial pulse wave transit time, which accounts for a patient's pre-ejection period (PEP) when calculating changes in blood pressure. The parameter calculation system 100 can therefore more accurately determine when an occlusive blood pressure measurement is appropriate.

In the depicted embodiment, the parameter calculation system 100 includes a parameter calculator 110 and a display 120. The parameter calculator 110 can include hardware (such as one or more processors), software, and/or firmware for measuring a physiological parameter such as blood pressure. Inputs to the parameter calculator 110 can include, among others, optical sensor data provided by an optical sensor 102, acoustic sensor data provided by one or more acoustic sensors 104, and/or additional sensor data provided by one or more additional sensors 106. The optical sensor 102 can be a pulse oximetry sensor, a co-oximetry sensor, or the like. The acoustic sensors 104 can be biological sound sensors. The biological sounds may include heart, breathing, and/or digestive system sounds, in addition to many other physiological phenomena. The additional sensors 106 can include any sensing device that provides physiological data to the parameter calculator 110. For example, the additional sensors 106 can include an electrical sensor configured to provide an ECG signal, an acoustic sensor, and/or a bioimpedance sensor, or any other sensing device.

The optical sensor 102 can use spectrophotometry techniques to measure a variety of blood constituents, including for example, oxygen saturation, hemoglobin, methemoglobin, carboxyhemoglobin, other hemoglobin species, concentrations of the same, and the like. In addition, the optical sensor 102 can also be used to measure a variety of other physiological parameters, including pulse rate, perfusion, and the like. The optical sensor 102 can include one or more emitters that shine one or more wavelengths of light through tissue of a living person, such as through a finger, toe, or foot. One or more detectors can receive the transmitted light after attenuation by the tissue and can generate one or more signals responsive to the attenuated light.

In certain embodiments, the parameter calculator 110 derives a photoplethysmograph from the optical sensor data The photoplethysmograph (sometimes referred to herein as a "plethysmograph," "photopleth" or "pleth") can be a waveform that can represent changes in blood volume as measured by one or more wavelengths of light irradiated at a tissue site of a patient. The photoplethysmograph can be caused by arterial pulsation, and as such, can be related to arterial blood pressure. Thus, in some embodiments, the parameter calculator 110 uses the optical sensor data to derive an indication of blood pressure for a patient.

In one embodiment, the parameter calculator 110 can use the optical sensor data and the additional sensor data 106 to derive one or more indications of blood pressure. For example, a combination of the optical sensor data and data from electrical sensor(s), acoustic sensor(s) 104, and/or bioimpedance sensors(s) can be used to determine an amount of time that it takes for a pulse to travel through an artery from a patient's heart to a measurement site. This time can be referred to as an arterial pulse-wave transit time (a-PWTT). Advantageously, in certain embodiments, the parameter calculator 110 can more accurately determine the a-PWTT based at least in part on the additional sensor data 106 obtained from an acoustic (104) and/or bioimpedance sensor. In particular, using the additional sensor data 106, the parameter calculator 110 can account for a patient's cardiac pre-ejection period (PEP) when calculating a-PWTT. In other embodiments, the parameter calculator 110 uses the acoustic sensor data derived from acoustic sensors 104 alone to derive one or more indications of blood pressure. Using the estimated changes in blood pressure, the parameter calculator 110 can trigger a blood pressure cuff 108 to obtain an occlusive blood pressure measurement.

The parameter calculator 110 can output parameter data 113 indicative of the calculated parameters, including blood pressure, for presentation to a user. The parameter data 113 can be displayed on a display device 120. In another embodiment, the parameter calculator 110 provides parameter values as an output 112 to another device, for example, a device providing an audible response, or over a network to a remote device. For example, a remote device might be a computer located at a nurses' station or a clinician's handheld device.

The parameter calculator 110 can also calculate trend data reflecting trend information for the parameter data 113. The parameter calculator 110 can also synthesize or scale waveform data. In addition to outputting the parameter data 113, the parameter calculator 110 can output trend data 114, synthesized, scaled, or actual waveforms 115, calibration data 116, and alarms 117. The parameter calculator 110 can provide the outputs 113, 114, 115, 116 to the display 120, to a separate patient monitoring device, or to another device configured to receive physiological parameter information.

In an embodiment, the parameter calculator 110 is implemented in a single monitoring device. In an embodiment, the features of the parameter calculator 110 are distributed among separate devices. In an embodiment, the parameter calculator 110 includes a processor, processor board, or an Original Equipment Manufacture (OEM) board. In an embodiment, the parameter calculator 110 is portable. Data communicated between the various components of the parameter calculation system 100 can be communicated through cables or wirelessly. Other inputs and/or outputs can be included with the system 100.

The display 120 of the parameter calculation system 100 can be part of a patient monitor (not shown), which can also include other components, such as a speaker, power button, removable storage or memory (e.g., a flash card slot), an AC power port, and one or more network interfaces, such as a universal serial bus interface or an Ethernet port. The display 120 can indicate a measurement for blood pressure, for example, a measurement of the systolic and diastolic blood pressure in mmHg. Other physiological parameter values, waveforms, trend data, calibration data, alarms, and the like can also be output on the display 120.

Although the parameter calculator 110 is described as calculating changes in blood pressure, in some embodiments, the parameter calculator 110 calculates actual blood pressure values from the acoustic and/or additional sensor data. In addition, the parameter calculation system 100 can also measure other physiological parameters besides blood pressure, such as pulse rate, oxygen saturation ($SpO_2$), hemoglobin, total hemoglobin, hemoglobin species (e.g., methemoglobin, carboxyhemoglobin, or the like), carbon monoxide or dioxide, perfusion, and glucose, among a variety of other parameters.

Further, in some embodiments, the parameter calculator 110 uses acoustic sensor data (from the acoustic sensor(s) 104) to determine any of a variety of respiratory parameters of a patient, including respiratory rate, inspiratory time, expiratory time, inspiratory to expiratory (I:E) ratio, inspiratory flow, expiratory flow, tidal volume, minute volume, apnea duration, hypopnea duration, breath sounds (e.g., rales, rhonchi, and stridor), and changes in breath sounds such as decreased volume or change in airflow (either increase or decrease). In addition, in some cases the parameter calculator 110 monitors other physiological sounds from the acoustic sensor 104 data, such as heart rate (e.g., to help with probe off detection), heart sounds (S1, S2, S3, S4, and murmurs), and change in heart sounds such as normal to murmur or split heart sounds indicating fluid overload. Moreover, a second acoustic sensor 104 may be placed over the chest for better heart sound detection. The parameter calculator 110 may keep user inputs to a minimum (example, height) and use a Health Level 7 (HL7) interface to automatically input patient demography.

Example PWTT Calculations

Figure 2A:
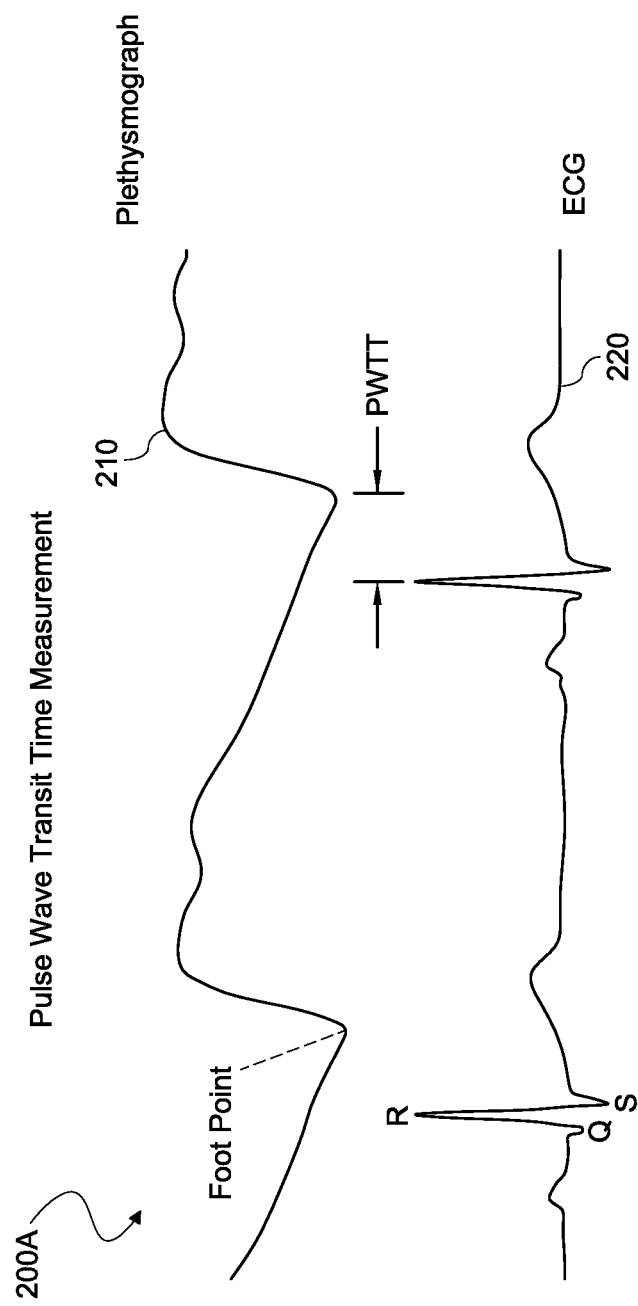
FIGS. 2A and 2B illustrate plots of plethysmograph and electrocardiograph (ECG) waveforms that can be used to calculate pulse wave transit time (PWTT)

FIG. 2A depicts an embodiment of a plot 200A that illustrates an example PWTT calculation. In the plot 200A, a plethysmograph waveform 210 and an ECG waveform 220 are shown. The plethysmograph waveform 210 can be obtained from an optical sensor 102 as described above. The ECG waveform 220 can be obtained from an electrical sensor.

The plethysmograph waveform 210 can reflect changes in pulsatile flow of blood in body tissue of a patient. The ECG waveform 220 can reflect electrical activity of a patient's heart. The ECG waveform 220 can have features including, for example, a Q-wave, an R-wave peak, and an S-wave, among others. A segment of the ECG waveform 220 from the Q point to the S point can be referred to as a QRS complex, which can represent ventricular activation.

Velocity of a blood pressure wave in the arteries has a correlation with blood pressure. As the length of an artery is typically constant or approximately constant, the time that it takes for the blood pressure wave to travel from the heart to an extremity can be used to derive an indication of blood pressure. In currently available monitoring systems, a measure of such time, referred to as PWTT, has been used to infer changes in blood pressure. In some embodiments, the PWTT can represent a difference in time between a feature of the plethysmograph waveform 210 and a feature of the ECG waveform 220. For example, in one embodiment, the PWTT can be obtained from the difference in time between the R-wave peak on the ECG waveform 220 and a foot point on the plethysmograph waveform 210. The foot point of the plethysmograph waveform 210 can correspond to the time of earliest onset of arrival of the pulse at a location away from the heart (e.g., at a patient's finger). In other embodiments, the PWTT can be obtained from the difference in time between either the Q-wave or the S-wave on the ECG waveform 220 and a feature on the plethysmograph waveform 210 (e.g., a foot point, peak, or some other feature).

Calculated in this manner from the plethysmograph and ECG waveforms 210, 220, PWTT can be fairly accurate for some patients. However, in some cases, using PWTT to measure changes in blood pressure provides inaccurate or unexpected results. At least a partial explanation of these unexpected results can be seen in FIG. 2B.

Figure 2B:
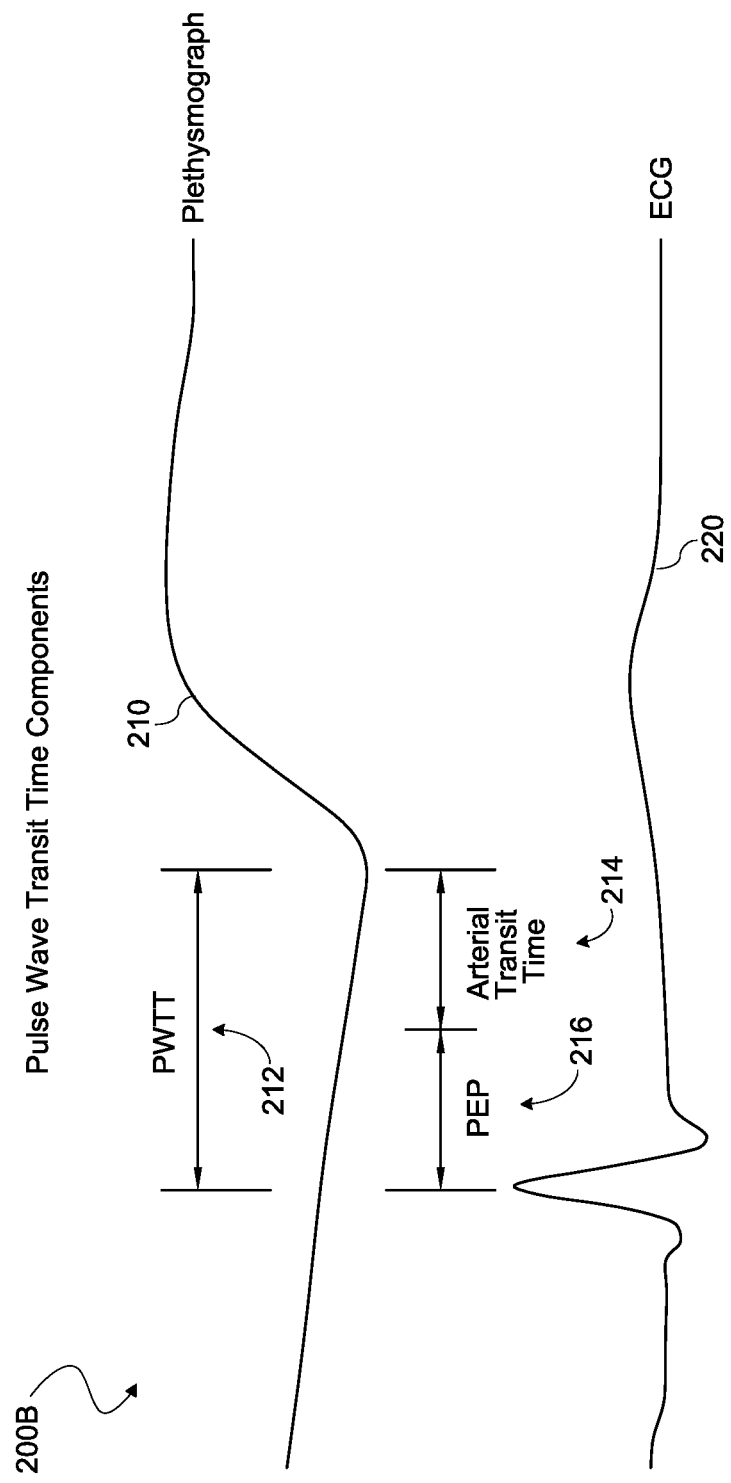

In FIG. 2B, an example plot 200 is shown that includes a plethysmograph waveform 210 and an ECG waveform 220. An overall PWTT 212 can be calculated from a point on the ECG waveform 220 to a point of the plethysmograph waveform 210, as described above. However, the overall PWTT 212 can actually include at least two components—an arterial pulse wave transit time (sometimes referred to as "a-PWTT") 214 and a pre-ejection period (PEP) 216.

The PEP 216 can be defined in different ways. For instance, in certain embodiments, the PEP 216 includes the difference in time between ventricular contraction and cardiac ejection of blood into the aorta. The PEP 216 can also be considered as a measured interval from the onset of ventricular depolarization, such as a Q-wave (or other feature) of an ECG, to the beginning of mechanical contraction of the heart muscle. For example, the PEP 216 can represent the difference in time from the onset of the QRS complex of the ECG signal 220 to when cardiac ejection actually occurs. Further, the PEP 216 can also be considered as the time interval from the beginning of the electrical activation of the ventricles to the opening of the aortic valve.

The value of the PEP 216 can fluctuate based on patient condition, age, sex, and medications taken by the patient, among possibly other factors. In some patients, the PEP 216 can account for a significant portion of the PWTT 212, including even as much as about 50% of the PWTT 212. Because PEP 216 can account for a significant portion of overall PWTT 212, including the PEP 216 in a PWTT measurement can result in inaccurate determinations of changes in a patient's blood pressure. In certain circumstances, this can even lead to not detecting a clinically significant change in blood pressure and not initiating an occlusive cuff measurement for confirmation. FIG. 2B also illustrates that it can prove difficult to derive the PEP 216 from a feature of a plethysmograph signal and a feature of an ECG signal.

Thus, in certain embodiments, the arterial PWTT 214, which accounts for the PEP 216, can more accurately correlate with changes in a patient's blood pressure than the overall PWTT 212. Thus, it can be advantageous to detect changes in the arterial PWTT 214 and to use these changes to trigger occlusive cuff measurements. The arterial PWTT 214 can be determined in some embodiments by calculating the PEP 216 and subtracting the PEP 216 value from the overall PWTT 212.

The PEP 216 can be derived, at least in part, from another physiological signal. Such a physiological signal can be indicative of cardiac ejection. Example physiological signals can include, but are not limited to, bioimpedance signals and acoustic signals. For example, in one embodiment, the PEP 216 can be derived from a feature of the ECG waveform 220 and a feature of another physiological signal. As another example, in another embodiment, the PEP 216 can be derived from a feature of the plethysmograph waveform 210 and a feature of another physiological signal. As yet another example, the PEP 216 can be accounted for by deriving arterial PWTT directly from a feature of an acoustic heart sound waveform and an acoustic waveform on an extremity, such as the hand, wrist, or limb.

Figure 2C:
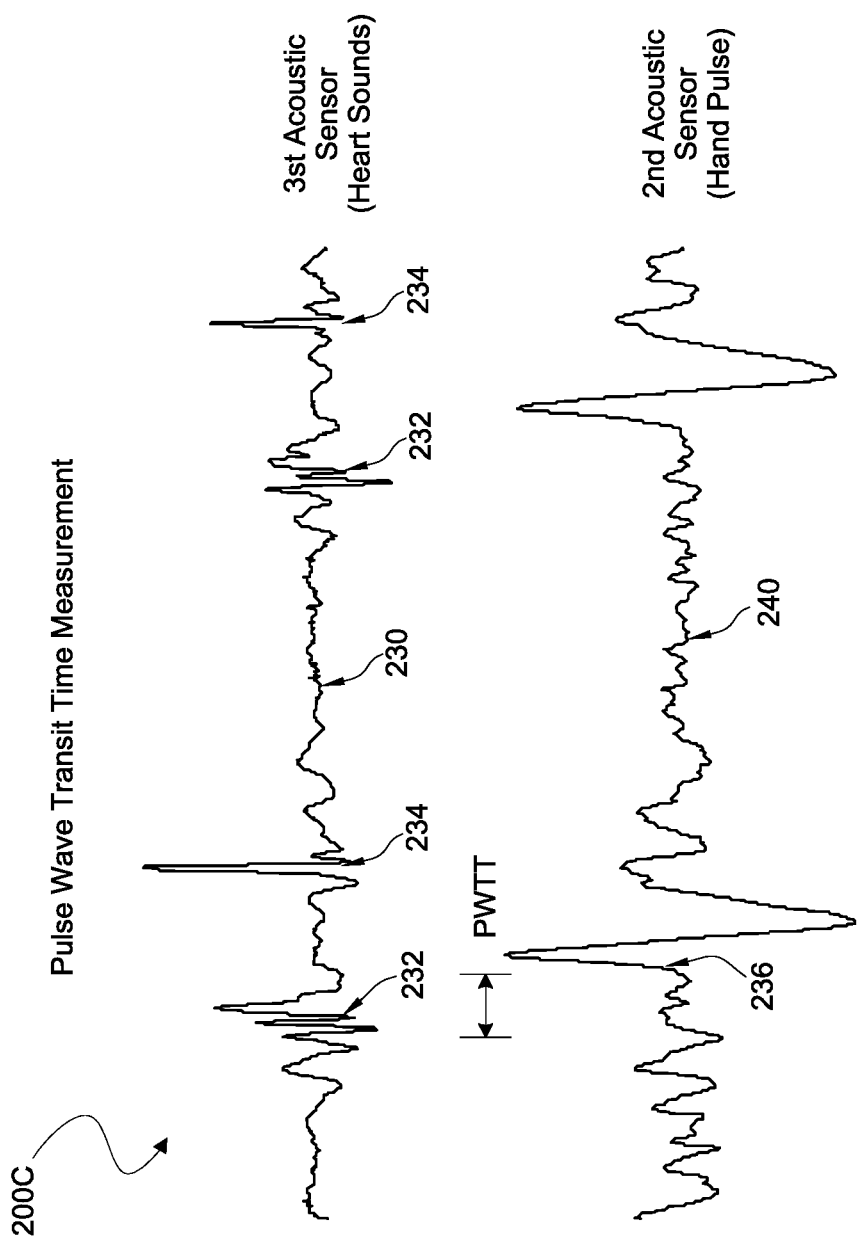
FIGS. 2C and 2D illustrate plots of acoustic waveforms that can be used to calculate PWTT.

FIG. 2C depicts an embodiment of a plot 200C that illustrates an example PWTT calculation that compensates for PEP using multiple acoustic sensors. In the plot 200C, a first acoustic waveform 230 and a second acoustic waveform 240 are shown. The first acoustic waveform 220 can be obtained from a first acoustic sensor positioned proximate a heart of a patient to monitor heart sounds of the patient. The heart sounds can be indicative of the closing of heart valves: the atrioventricular valves (mitral valve and tricuspid valve) and the semilunar valves (aortic valve and pulmonary valve). The closing of the heart valves corresponds to ventricular systole and diastole. The second acoustic waveform 240 can be obtained from a second acoustic sensor positioned at an arterial location away from the heart and configured to monitor peripheral pulse pressure wave vibrations or sounds at the arterial location. For example, the second acoustic sensor can be positioned proximate a wrist artery (e.g., radial artery, ulnar artery), proximate a carotid artery on the neck of the patient, or proximate an artery of the leg.

The first acoustic waveform 230 can include heart sounds of the patient corresponding to the closing of heart valves at the transition between ventricular systole and diastole. For example, the heart sounds can include first heart sounds (e.g., S1 heart sounds) 232 corresponding to the closure of the atrioventricular valves at the time ventricular systole begins and ventricular diastole ends and second heart sounds (e.g., S2 heart sounds) 234 corresponding to the closure of the aortic valve and the pulmonary valve at the time ventricular systole ends and ventricular diastole begins. The occurrence of the S1 heart sound can identify the start time of ejection of blood from the heart and the occurrence of the S2 heart sound can mark the end time or approximate end time of ejection of blood from the heart. Accordingly, the actual ejection of blood from the ventricles may occur for patients at the first heart sound (e.g., at the start, peak, or end of the first heart sound), between the start of the first heart sound (the S1 sound) and the start of the second heart sound (the S2 sound), or at the second heart sound (e.g., start, peak, or end of the second heart sound).

The second acoustic waveform 240 can include an arterial pulse at a second location remote from the heart (e.g., at a patient's wrist or neck). The second acoustic waveform 240 shown in FIG. 2C includes audio information of the peripheral arterial pulse at a patient's wrist, hand, or arm (or foot, ankle, or leg). For convenience, although the peripheral arterial pulse can be detected at a variety of locations on the body, the wrist will be used as an illustrative example for the remainder of this specification. The second acoustic waveform 240 may display a pressure wave received at the patient's wrist some time prior to actual arrival of the blood at the periphery.

In some embodiments, the arterial PWTT can represent a difference in time between a feature of the first acoustic waveform (e.g., heart sounds waveform) and a feature of the second acoustic waveform (e.g., wrist pulse waveform). For example, in one embodiment, the arterial PWTT can be obtained from the difference in time between a feature of the first heart sound (the S1 sound) 232 on the acoustic heart sounds waveform 240 (e.g., start, maximum peak, end, some other feature of the S1 sound 242) and a feature of the acoustic wrist pulse waveform 220 (e.g., bottom onset or upstroke point 246 of the waveform 220 or start, maximum peak, end, some other feature of the waveform 220). In other embodiments, the arterial PWTT can be obtained from the difference in time between a determined centroid location of the S1 sound 232 or a location of the centroid of the energy from the start of the S1 sound 232 until the start of the S2 sound 234 and a feature on the acoustic wrist pulse waveform (e.g., a bottom onset, a foot point, a peak, or some other feature). In some embodiments, the envelope of the waveform 220 is obtained and used in the analysis described herein, e.g., by finding a feature of the envelope rather than the waveform 220 itself.

In one embodiment, the arterial PWTT can be obtained from the difference in time from a location between the S1 and S2 heart sounds 232, 234 and/or between a centroid of the energy of the S1 and S2 sounds 232, 234 and the bottom onset of a corresponding pulse of an acoustic arterial pulse waveform (e.g., an acoustic wrist pulse waveform or an acoustic carotid pulse waveform). In some embodiments, an arterial PWTT determination based on identified features of two mechanical acoustic waveforms advantageously provides a more stable result than a PWTT determination based on an identified feature of an electrical waveform (e.g., ECG waveform) and an identified feature of a mechanical waveform (e.g., photoplethysmograph waveform).

Figure 2D:
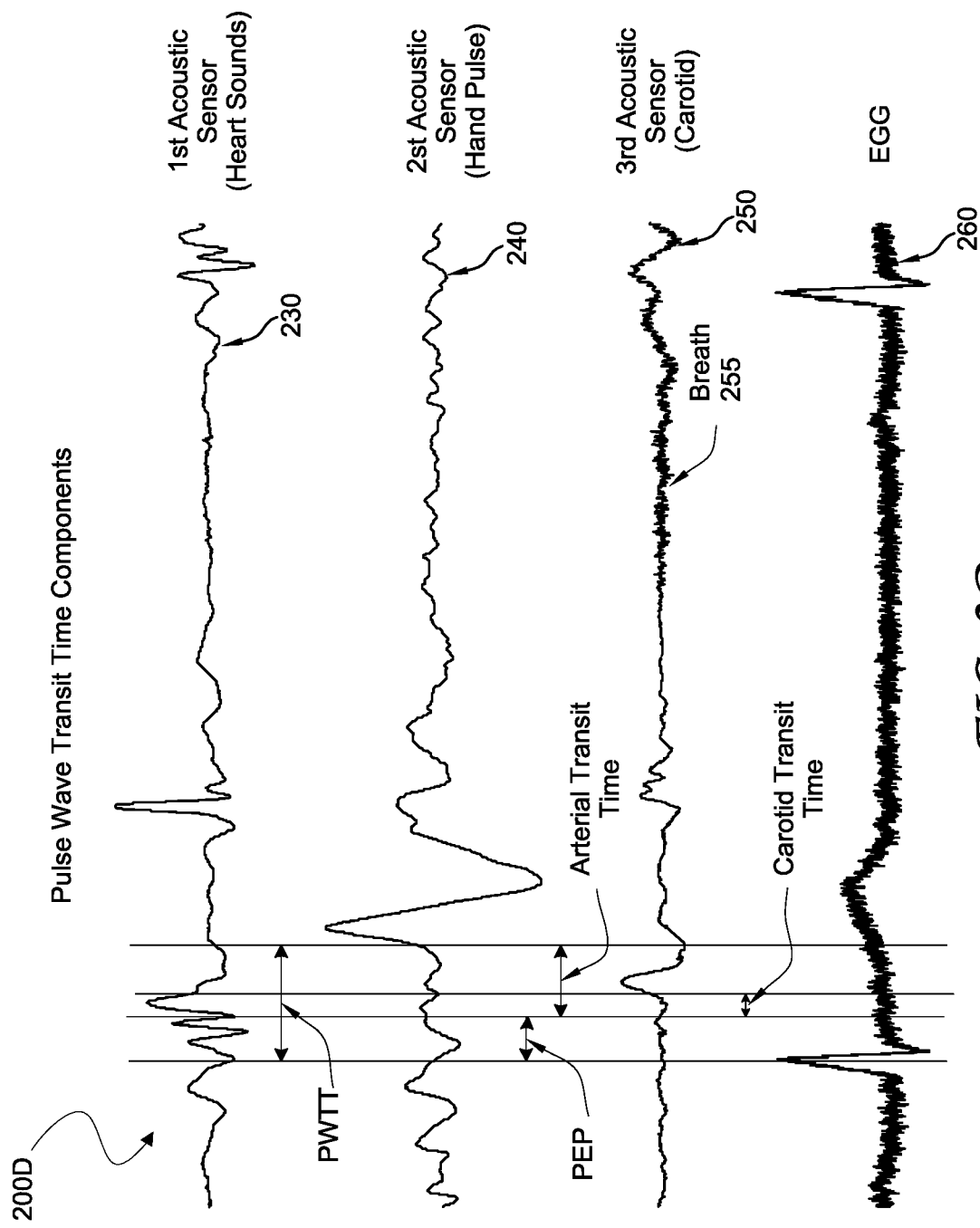

Turning to FIG. 2D, a plot 200D is shown that includes a set of four example waveforms. The acoustic heart sounds waveform 230 and the acoustic wrist pulse waveform 240 are illustrated again, along with a third acoustic waveform (an acoustic carotid pulse waveform) 250 and an ECG waveform 260. The plot 200D helps to illustrate the two components that make up an overall PWTT measurement in certain embodiments: a pre-ejection period (PEP) component and an arterial transit time component. The use of two acoustic sensors results in PWTT or time-difference-of-arrival calculations that, in certain embodiments, more accurately reflect arterial pulse wave transit time, thereby allowing blood pressure measurements to be taken more efficiently.

The acoustic carotid pulse waveform 250 can help to provide another measurement indicator (e.g., a control or reference or another input component) that can be used to determine the arterial pulse wave transit time or other arterial properties because the distance is known between the two sensors. The acoustic carotid pulse waveform 250 or any of the other waveforms can provide an indication of patient breathing, as shown by the presence of noise 255 on the acoustic carotid pulse waveform 250. In some implementations, the acoustic carotid pulse waveform 230 can be used in place of the wrist pulse waveform 240 to determine the arterial PWTT.

In some embodiments, the PEP is derived from one or more features of one or more acoustic signals. In one embodiment, the PEP is determined from the time of the start of the S1 heart sound 232 to the time of the end of the S1 heart sound 232. In other embodiments, the PEP can be derived from a feature of an ECG waveform 260 and a feature of another physiological signal (e.g., a pleth signal or an acoustic signal). One way to measure PEP is to determine the difference between an R wave peak of the ECG waveform 260 and a feature of the S1 sound 212 on the acoustic heart sounds waveform 230 (e.g., a foot point, peak, centroid, or other feature or derived location). More generally, PEP can be determined as a difference in time between any feature of the ECG waveform 260 and any feature of the acoustic heart sounds waveform 230, including in some embodiments, a feature of the S2 heart sound 234. The PEP can vary depending on patient pathology, and a determination of PEP can provide information regarding heart conditions to a clinician. In some embodiments, PEP is not calculated or used at all by the parameter calculation system 100 because the arterial PWTT is determined by the acoustic sensors.

Figure 3:
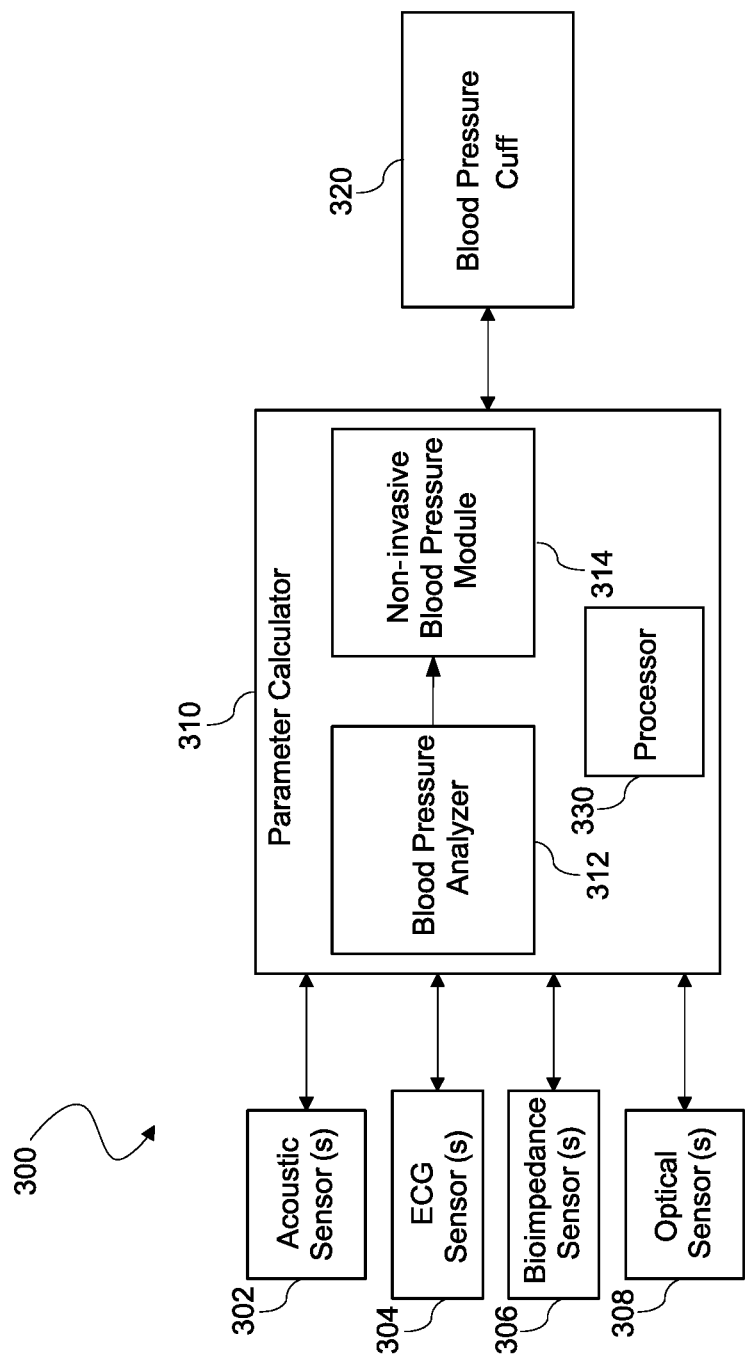
FIG. 3 illustrates another embodiment of a blood pressure monitoring system.

FIG. 3 illustrates an embodiment of a blood pressure monitoring system 300 that can determine PWTT measurements (including a-PWTT measurements) from signals received from various sensors. The blood pressure monitoring system 300 can implement certain features of the parameter calculation system 100 described above. In particular, the system 300 can periodically measure blood pressure using a blood pressure cuff 320, which can be an automatic occlusive cuff or the like. In addition, the system 300 can perform PWTT calculations to noninvasively detect changes in a patient's blood pressure. The illustrated blood pressure monitoring system 300 includes sensors and associated modules that can advantageously be used to monitor blood pressure. The depicted modules can be implemented in hardware and/or in software (e.g., as executed by one or more processors 330 or computing devices).

In the depicted embodiment, the system 300 includes a parameter calculator 310, which can be implemented in hardware and/or software. The parameter calculator 310 is a more detailed implementation of the parameter calculator 110 of FIG. 1 and can include all the features thereof. Various sensors communicate with the parameter calculator 310. These sensors include two or more acoustic sensors 302, one or more ECG sensors 304, one or more bioimpedance sensors 306, and one or more optical sensors 308. The acoustic sensors 302 can include piezoelectric transducers or other acoustic transducers for measuring a patient's body sounds, such as breathing and heart sounds. The ECG sensor(s) 304 can include ECG leads or the like for measuring the electrical activity of the heart. The bioimpedance sensor(s) 306 can include electrodes placed on the neck and/or thorax for measuring the impedance of electrical signals in the body. More detailed embodiments of these sensors are described below with respect to FIGS. 5-8.

The example parameter calculator 310 shown includes a blood pressure analyzer 312 and a noninvasive blood pressure module 314. The blood pressure analyzer 312 can calculate arterial PWTT using the outputs of some or all of the various sensors 302, 304, 306, and 308. Based at least in part on this calculated PWTT, the blood pressure analyzer 312 can send a trigger signal to the noninvasive blood pressure module 314. In response to receiving this trigger signal, the non-invasive blood pressure module 314 can cause the blood pressure cuff 320 to take a blood pressure measurement. In some embodiments, the non-invasive blood pressure module 314 is a separate component from the parameter calculator 310, for example, on an Original Equipment Manufacture (OEM) board or the like.

In one embodiment, the acoustic sensor 302 is placed over the heart or near the heart of a patient so as to detect heart sounds of the patient. The acoustic sensor 302 can be positioned on the chest, back, neck, side, abdomen, or other area of the body so as to detect the heart sounds. Heart sounds can include, among others, first and second heart sounds. The first heart sound can correspond to systole, or the contraction of the ventricles and corresponding ejection of blood from the heart. PEP can therefore be measured as a time difference between a feature of the ECG waveform derived from the electrical sensor(s) 304 and a first heart sound feature of an acoustic waveform derived from the acoustic sensor 302. The second heart sound can correspond to the beginning of diastole.

For example, referring to FIG. 4A, an example acoustic waveform 410 and ECG waveform 412 are shown that illustrate one possible PEP calculation. The acoustic waveform 410 includes peaks 422, 424 that correspond to example first and second heart sounds, respectively. The ECG waveform 412 includes a peak 432 corresponding to the R wave of the QRS complex. One way to measure PEP is to determine the difference between the R wave peak 432 and the first heart sound peak 422. In another embodiment, the PEP is measured as a difference between the R wave peak 432 and a foot 423a or 423b of the acoustic waveform 410. More generally, PEP can be determined as a difference in time between any feature of the ECG waveform 412 and any feature of the acoustic waveform 410, including in some embodiments, a feature of the second heart sound peak 424.

Referring again to FIG. 3, PWTT measurements (e.g., PEP or a-PWTT measurements) can also be calculated using the one or more bioimpedance sensors 306. The bioimpedance sensors 306 can implement principles of impedance cardiography, which can also be referred to as thoracic electrical bioimpedance. The bioimpedance sensors 306 can measure the impedance of a patient's chest cavity by injecting alternating (or direct) current through the patient's chest. The current tends to seek the path of least resistance, which is the patient's blood-filled aorta. The blood volume and velocity in the aorta can change with each heartbeat, resulting in corresponding changes in impedance measured by the bioimpedance electrodes. These changes in impedance can be used to derive PEP.

For instance, referring to FIG. 4B, an example bioimpedance waveform 440 is shown together with the ECG waveform 412 of FIG. 4A. The bioimpedance waveform includes a peak 442 that corresponds to a peak change in impedance with respect to time. This peak 442 can correspond to ejection of blood from the heart, corresponding to a current change in the aorta resulting from a heartbeat. Thus, PEP can be measured between a feature of the ECG waveform 412 and a feature of the bioimpedance waveform 440. For instance, PEP can be measured between the R wave peak 432 and a foot point 444 of the bioimpedance waveform 440. This foot point 444 is sometimes referred to as the "B" point of the bioimpedance waveform 440 and corresponds to the maximum rate of change of the waveform 440. The PEP can also be measured from the R wave peak 432 (or another feature of the ECG waveform 412) and the peak 442 of the bioimpedance waveform.

Thus, in certain embodiments, the acoustic and/or bioimpedance sensors 302, 306 of FIG. 3 can be used in conjunction with the ECG sensor(s) 304 to calculate PEP. In some implementations, only an acoustic sensor 302 and ECG sensor(s) 304 are used to calculate PEP. Other implementations employ only bioimpedance sensor(s) 306 and ECG sensor(s) 304 to calculate PEP. Still other embodiments of the system 300 can calculate PEP using acoustic sensor(s) 302 and separately calculate PEP using bioimpedance sensor(s) 306. The blood pressure analyzer 312 can average or otherwise combine the PEP calculations from these different sensors 302, 306 in some embodiments.

In other implementations, two acoustic sensors 302 of FIG. 3 are used to calculate PWTT measurements (e.g., a-PWTT or PEP measurements). In some implementations, multiple techniques can be used to calculate PEP or a-PWTT. In some embodiments, the blood pressure analyzer 312 can average or otherwise combine the PWTT calculations from these different sensors. In other embodiments, PWTT measurements obtained from the one or more of the sensors can be used to assess confidence in the PWTT measurements obtained from other of the sensors. Additional details will be further described below in connection with FIGS. 9A-9C.

Figure 5A:
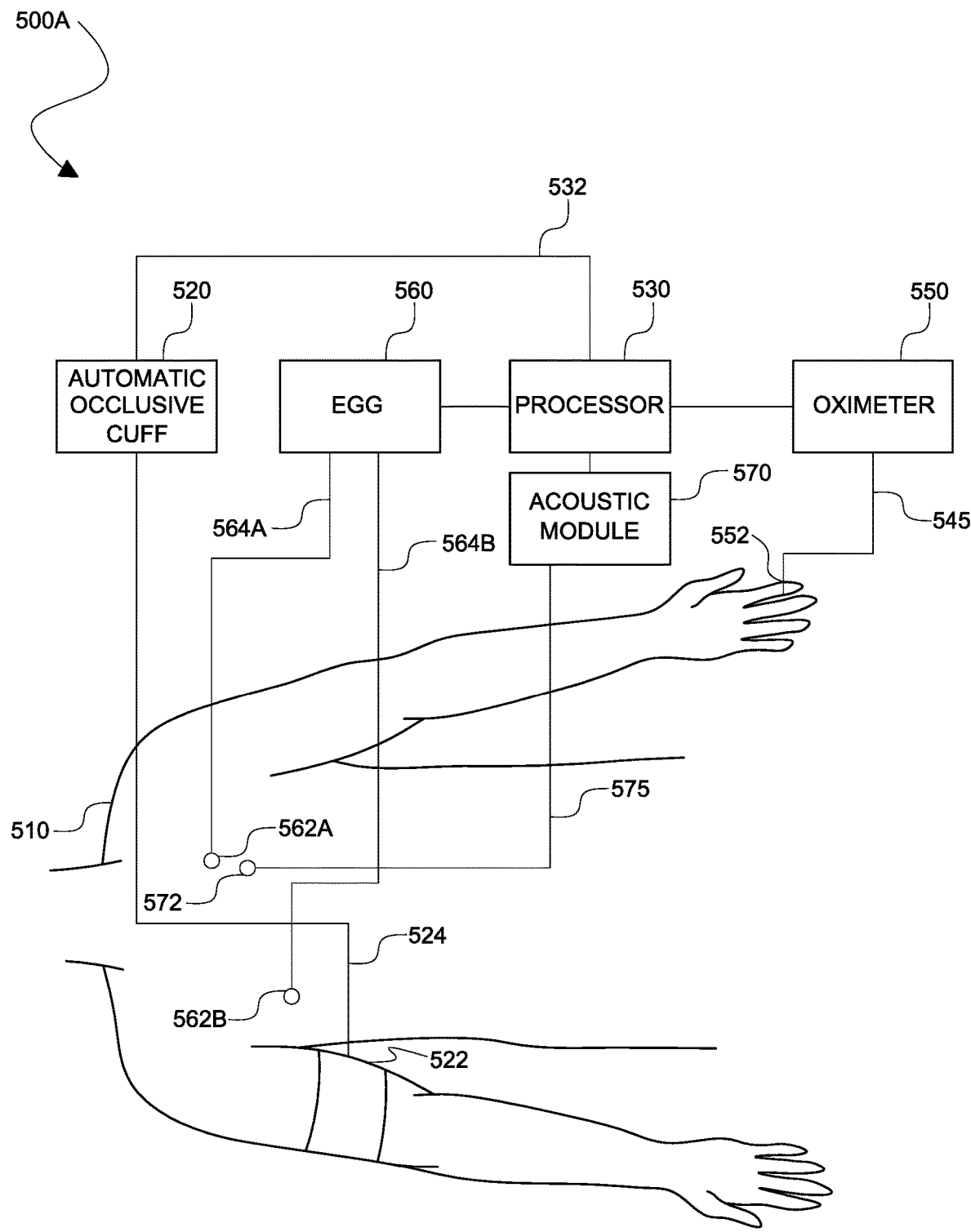
FIGS. 5A and 5B illustrate embodiments of blood pressure monitoring systems coupled to a patient.

FIG. 5A illustrates a more detailed embodiment of a blood pressure monitoring system 500A including an acoustic sensor coupled to a patient. The blood pressure monitoring system 500A can implement certain features of the blood pressure monitoring system 300 and parameter calculation system 100 described above. The illustrated blood pressure monitoring system 500A includes sensors, associated modules, and a processor 530 that can advantageously be used to monitor blood pressure. The depicted modules can be implemented in hardware and/or in software (e.g., as executed by the processor 530).

The illustrated blood pressure monitoring system 500A is coupled to a patient 510. The patient 510 is shown with a cuff 522 attached to an upper arm. The cuff 522 can be implemented in combination with an automatic occlusive cuff control unit 520. The cuff 522 can be in communication with the automatic occlusive cuff control unit 520 via a cable 524. The control unit 520 can control the inflation of the cuff 522 and receive signals from the cuff 522 regarding systolic and diastolic blood pressure.

In addition to the automatic occlusive cuff, ECG sensors 562A and 562B can be coupled to the patient 510. The ECG sensors 562A, 562B can provide any of the ECG signals described above. The ECG sensors 562A and 562B can be implemented as dual electrodes or split electrodes. While the illustrated blood pressure monitoring system includes two ECG sensors 562A and 562B, in other embodiments, only one ECG sensor can be coupled to patient 510. In yet other embodiments, more than two ECG sensors can be coupled to the patient 510, such as three or more sensors. In addition, ECG sensors can be placed at different measurement site(s) than illustrated in FIG. 5A. For example, one or more ECG sensors could be coupled to the back of the patient 510.

The illustrated ECG sensors 562A, 562B can be coupled to an ECG unit 560 via cables 564A and 564B, respectively. The ECG unit 560 can interface with the ECG sensors 562A, 562B and provide an ECG signal to the processor 530. In some embodiments, the ECG unit can convert and output of ECG sensors 562A, 562B from an analog signal to a digital signal and/or perform other pre-processing. The ECG unit 560 can be implemented separate from the processor 530 or alternatively as part of the processor 530.

An optical sensor 552 can also be coupled to the patient 510. The optical sensor 552 can provide any of the plethysmograph waveforms illustrated in FIGS. 2A and 2B and/or the optical sensor data 104 described above in connection with FIG. 1. The illustrated optical sensor 552 can be coupled to oximeter unit 550 via cable 554. The oximeter unit 560 can interface with the optical sensor 552 and provide an optical signal to the processor 530. In some embodiments, the oximeter unit 550 can convert and output of optical sensor 552 from an analog signal to a digital signal and/or perform other pre-processing. The oximeter unit 550 can be implemented separate from the processor 530 or alternatively as part of the processor 530. It should be noted that in certain embodiments, the optical sensor 552 can provide data to a monitor other than a pulse oximeter.

An acoustic sensor 572 can also be coupled to the patient 510. The acoustic sensor 552 can provide any of the acoustic signals and waveforms described above. The illustrated acoustic sensor 572 is coupled to the patient 510 at a measurement site near the patient's heart. In other embodiments, the acoustic sensor can be coupled to the patient 510 at different measurement sites, so long as the acoustic sensor can provide useful information indicative of cardiac ejection. In other embodiments, more than one acoustic sensor 572 can be used. More detail regarding the acoustic sensor 572 will be provided below in connection with FIG. 6.

The acoustic module 570 can be coupled to the acoustic sensor 572 via cable 574. The acoustic module 570 can interface with the acoustic sensor 572 and provide an acoustic signal to the processor 530. In some embodiments, the acoustic module can convert and output of the acoustic sensor 572 from an analog signal to a digital signal and/or perform other pre-processing. The acoustic module 570 can be implemented separate from the processor 530 or alternatively as part of the processor 530.

The processor 530 can advantageously be used to measure indicators of blood pressure, such as PWTT, PEP, and/or arterial PWTT, using information provided by the ECG unit 560, the oximeter unit 550, and the acoustic module 570. The processor 530 can include, for example, one or more microprocessors, microcontrollers, cores, digital signal processors (DSPs), or the like. The processor 530 can store instructions in a computer-readable medium. The processor 530 can also perform other operations for the blood pressure monitoring system 500A that are not explicitly described herein.

The processor 530 can also be coupled to the automatic occlusive cuff control unit 520 via line 532. The processor 530 can receive information regarding a blood pressure measurement of the patient 510 from the automatic occlusive cuff control unit 520, and can activate the automatic occlusive cuff control unit 520 via the line 532.

In certain embodiments, the processor 530 determines the arterial PWTT, compensated for PEP, using the acoustic sensor 572, the ECG sensors 562A, and the optical sensor 552. The processor 530 can track changes in this arterial PWTT and trigger the automatic occlusive cuff control unit 520 to take a blood pressure measurement with the cuff 522. The PEP-compensated arterial PWTT calculations can be more accurate than currently-available PWTT calculations that do not take PEP into account. Thus, in certain embodiments, the blood pressure monitoring system 500A can more effectively monitor the patient's 510 blood pressure with potentially greater comfort for the patient 510.

Figure 5B:
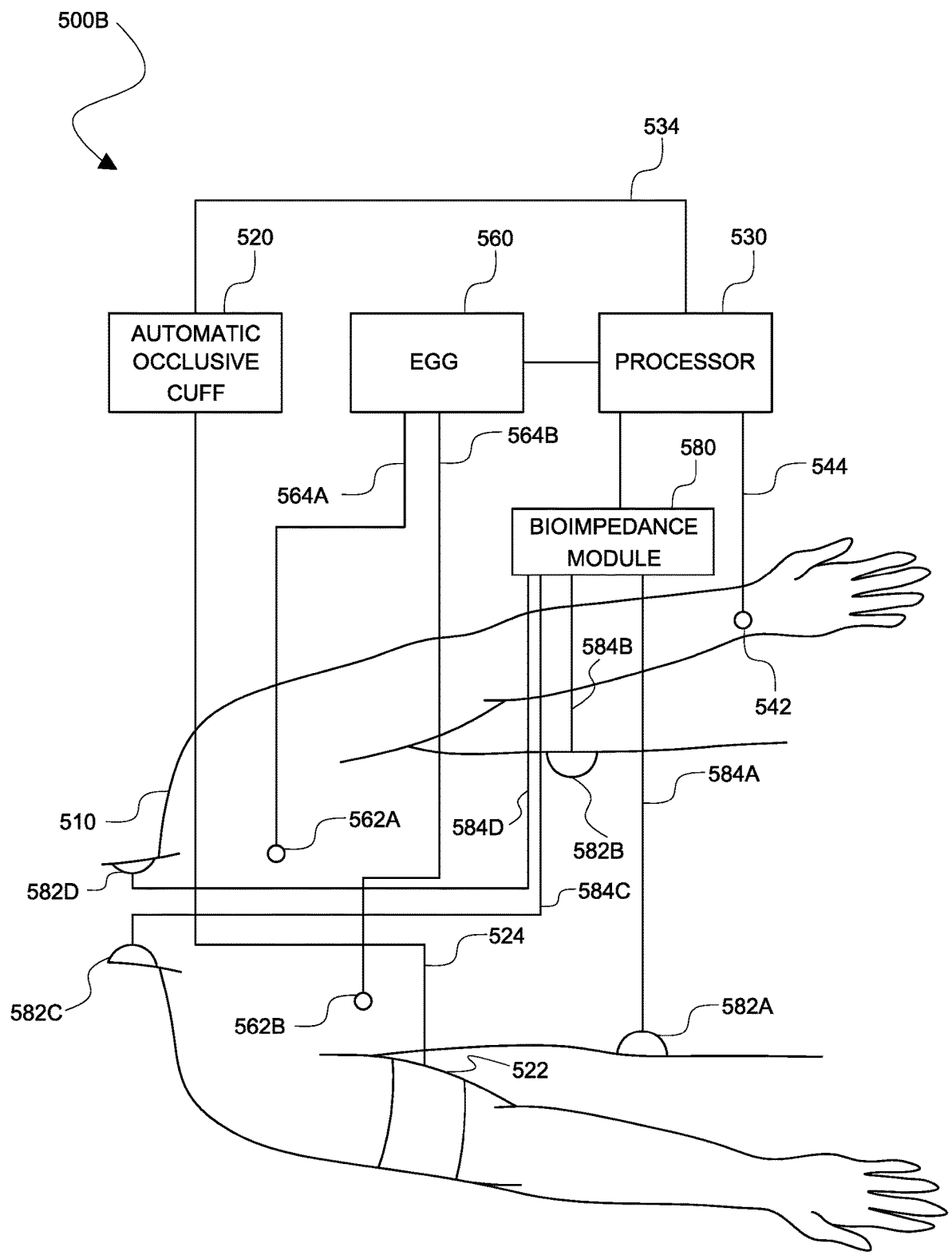

FIG. 5B illustrates another embodiment of a blood pressure monitoring system 500B including bioimpedance sensors 582 coupled to the patient 510. The blood pressure monitoring system 500B can implement certain features of the blood pressure monitoring system 300 and parameter calculation system 100 described above. The illustrated blood pressure monitoring system 500B can be substantially similar to the blood pressure monitoring system 500A of FIG. 5A. However, bioimpedance sensors 582A, 582B, 582C, 582D and a bioimpedance module 580 are included in place of the acoustic sensor 572 and the acoustic module 570.

The bioimpedance sensors 582A, 582B, 582C, 582D can be coupled to the patient 510 at various measurement sites. For example, as illustrated, two bioimpedance sensors 582A and 582B can be coupled to the sides of the patient 510 and two bioimpedance sensors 582C and 582D can be coupled to the neck of the patient 510. Other suitable measurement sites can be used in other embodiments. The bioimpedance sensors 582A, 582B, 582C, 582D can be used to provide the bioimpedance waveforms described above with respect to FIG. 4B and/or any of the additional sensor data 106 described above in connection with FIG. 1. Suitable bioimpedance sensors 582 can include electrodes or the like.

The bioimpedance unit 580 can be coupled to one or more of the bioimpedance sensors 582A, 582B, 582C, 582D via one or more cables 584A, 584B, 584C, 584D, respectively. The bioimpedance unit 580 can interface with one or more of the bioimpedance sensors 582A, 582B, 582C, 582D and provide one or more bioimpedance signals to the processor 530. In some embodiments, the bioimpedance unit 580 can convert an output of one or more of the bioimpedance sensors 582A, 582B, 582C, 582D from an analog signal to a digital signal and/or perform other pre-processing. The bioimpedance unit 580 can be implemented separate from the processor 530 or alternatively as part of the processor 530.

In certain embodiments, the processor 530 determines the arterial PWTT, compensated for PEP, using the bioimpedance sensors 582, the ECG sensors 562A, 562B and the optical sensor 552. The processor 530 can track changes in this arterial PWTT and trigger the automatic occlusive cuff control unit 520 to take a blood pressure measurement with the cuff 522. The PEP-compensated arterial PWTT calculations can be more accurate than currently-available PWTT calculations that do not take PEP into account. Thus, in certain embodiments, the blood pressure monitoring system 500B can more effectively monitor the patient's 510 blood pressure with potentially greater comfort for the patient 510.

Although shown separately for ease of illustration, in certain embodiments the ECG sensors 562A, 562B and the bioimpedance sensors 582 can be combined. For instance, the bioimpedance sensors 582 can obtain ECG data in some implementations, and vice versa.

FIG. 6 illustrates example positioning locations for the acoustic sensors that can be used in the various systems and methods described herein (such as the parameter calculation system 100 and the blood pressure monitoring system 300). As described above, a first acoustic sensor 602 can be placed over the heart or near the heart of a patient so as to detect heart sounds of the patient. In some embodiments, the acoustic heart sounds sensor 602 can be positioned over the heart in or near the second intercostal space; however, the acoustic heart sounds sensor 602 can be positioned at other locations (such as the chest, back, neck, side, abdomen, or other area of the body) so as to more accurately detect particular heart sounds (e.g., the S1 and S2 sounds). In some implementations, the acoustic heart sounds sensor 602 can be positioned at a location at which both the S1 and S2 heart sounds can be effectively measured. In other implementations, the acoustic heart sounds sensor 602 can be positioned at a location configured to obtain increased signal strength for a particular heart sound without regard to other heart sounds.

With continued reference to FIG. 6, a second acoustic sensor 604 can be placed at or near an artery on or near the wrist of a patient to measure an arterial pulse at a distance from the heart. For example, the second acoustic sensor 604 can be placed over the ulnar artery or the radial artery to obtain information indicative of a wrist pulse. A third acoustic sensor 606 can be placed on a neck of a patient at a location over or near a carotid artery to obtain information indicative of a carotid pulse. In some implementations, all three acoustic sensors are used. In other implementations, only the acoustic heart sounds sensor 602 and one of the other two sensors are used. The sensors of FIG. 6 can be coupled to a parameter calculation system (e.g., the parameter calculation system 100 or the blood pressure monitoring system 300). FIG. 6 merely illustrates example locations for the types of sensors that can be used in various implementations; other suitable locations may also be used.

Figure 7:
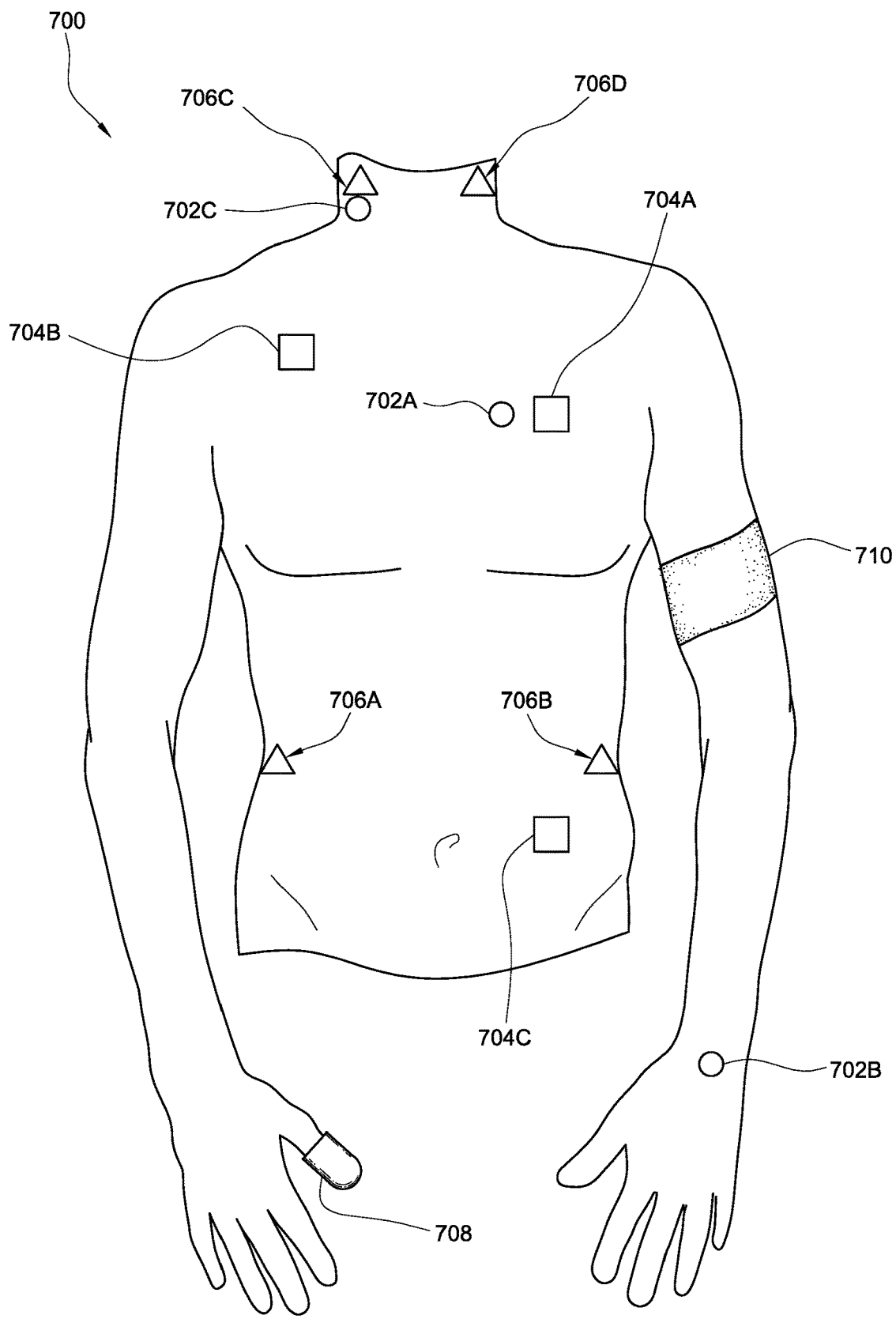
FIG. 7 illustrates example positioning locations for acoustic, electrocardiograph (ECG), optical and bioimpedance sensors that can be used in the various systems and methods described herein.

FIG. 7 illustrates example positioning locations for acoustic, electrocardiograph (ECG), bioimpedance and optical sensors that can be used in the various systems and methods described herein (such as the blood pressure monitoring system 300). The acoustic sensors 702A-702C are illustrated as circles, the ECG sensors 704A-704C are illustrated as squares, and the bioimpedance sensors 706A-706D are illustrated as triangles. FIG. 7 also illustrates an optical sensor 708 and an occlusive blood pressure cuff 710. The sensors of FIG. 7 can be coupled to a blood pressure monitoring system (e.g., the blood pressure monitoring system 300). Although FIG. 7 illustrates multiple sensors and multiple positioning locations, all of the sensors and/or positioning locations need not be used; FIG. 7 merely illustrates example locations for the types of sensors that can be used in various implementations. The number, locations, and type of sensors used can vary.

The blood pressure cuff 710 can be attached to an upper arm. The cuff 710 can be implemented in combination with an automatic occlusive cuff control unit (not shown). The cuff 710 can be in communication with the automatic occlusive cuff control unit via a cable and/or hose. The control unit can control the inflation of the cuff 710 and receive signals from the cuff 710 regarding systolic and diastolic blood pressure.

The acoustic sensors 702A-702C can be coupled to an acoustic module (not shown) via one or more cables or wirelessly. The acoustic module can interface with the acoustic sensors 702A-702C and provide acoustic signals to the processor 330. In some embodiments, the acoustic module can convert an output of the acoustic sensors 702A-702C from an analog signal to a digital signal and/or perform other pre-processing. The acoustic module can be implemented separate from the processor 330 or alternatively as part of the processor 330 or even as part of one or more of the sensors 702A-702C.

The ECG sensors 704A-704C can provide any of the ECG signals described herein. The ECG sensors 704A-704C can be implemented as dual electrodes or split electrodes. While the patient 700 in FIG. 7 has three ECG sensors 704A-704C, in other embodiments, only one ECG sensor or two ECG sensors can be coupled to the patient 700. In yet other embodiments, more than three ECG sensors can be coupled to the patient 700, such as four or more sensors. In addition, ECG sensors can be placed at different measurement site(s) than illustrated in FIG. 7. For example, one or more ECG sensors could be coupled to the back of the patient 700.

The illustrated ECG sensors 704A-704C can be coupled to an ECG unit (not shown) via cables or wirelessly. The ECG unit can interface with the ECG sensors 704A-704C and provide an ECG signal to a processor 330. In some embodiments, the ECG unit can convert an output of ECG sensors 704A-704C from an analog signal to a digital signal and/or perform other pre-processing. The ECG unit can be implemented separate from the processor 330 or alternatively as part of the processor 330.

The bioimpedance sensors 706A-706D can be coupled to the patient 700 at various measurement sites. For example, as illustrated, two bioimpedance sensors 706A and 706B can be coupled to the sides of the patient 700 and two bioimpedance sensors 706C and 706D can be coupled to the neck of the patient 700. Other suitable measurement sites can be used in other embodiments. The bioimpedance sensors 706A-706D can be used to provide bioimpedance waveforms that can be used in determining measurements indicative of blood pressure (e.g., overall PWTT, PEP, arterial PWTT). Suitable bioimpedance sensors 706A-706D can include electrodes or the like.

The bioimpedance sensors 706A-706D can be coupled to a bioimpedance unit (not shown). The bioimpedance unit can interface with one or more of the bioimpedance sensors 706A-706D and provide one or more bioimpedance signals to the processor 330. In some embodiments, the bioimpedance unit can convert an output of one or more of the bioimpedance sensors 706A-706D from an analog signal to a digital signal and/or perform other pre-processing. The bioimpedance unit can be implemented separate from the processor 330 or alternatively as part of the processor 330.

Although shown separately for ease of illustration, in certain embodiments the ECG sensors 704A-704C and the bioimpedance sensors 706A-706D can be combined. For instance, the bioimpedance sensors 706A-706D can obtain ECG data in some implementations, and vice versa.

An optical sensor 708 can also be coupled to the patient 700 (e.g., to a patient's finger). The illustrated optical sensor 708 can be coupled to an oximeter unit (not shown) via a cable or wirelessly. The oximeter unit can interface with the optical sensor 708 and provide an optical signal to a processor 330. In some embodiments, the oximeter unit can convert an output of optical sensor 708 from an analog signal to a digital signal and/or perform other pre-processing. The oximeter unit can be implemented separate from the processor 330 or alternatively as part of the processor 330. It should be noted that in certain embodiments, the optical sensor 708 can provide data to a monitor other than a pulse oximeter.

The processor 330 of FIG. 3 can advantageously be used to measure indicators of blood pressure, such as PWTT, PEP, and/or arterial PWTT, using information provided by the acoustic module, the ECG unit, the oximeter unit, and/or the bioimpedance unit. The processor 330 can include, for example, a microprocessor, microcontroller, a core, a digital signal processor (DSP), or the like. The processor 330 can store instructions in a computer-readable medium. The processor 330 can also perform other operations for the blood pressure monitoring system 300 that are not explicitly described herein.

The processor 330 can also be coupled to the automatic occlusive cuff control unit. The processor 330 can receive information regarding a blood pressure measurement of the patient 700 from the automatic occlusive cuff control unit, and can activate the automatic occlusive cuff control unit.

In certain embodiments, the processor 330 determines the arterial PWTT, using two of the acoustic sensors 702A-702C, independently or in conjunction with an additional acoustic sensor, one or more of the ECG sensors 704A-704C, one or more bioimpedance sensors 706A-706D, and the optical sensor 708. In some embodiments, the processor 330 determines the arterial PWTT using a combination of one or more acoustic sensors and one or more non-acoustic sensors (for example, using two bioimpedance sensors and one acoustic sensor). The processor 330 can track changes in this arterial PWTT and trigger the automatic occlusive cuff control unit to take a blood pressure measurement with the cuff 710. The arterial PWTT calculations obtained can be more accurate than currently-available PWTT calculations that do not take PEP into account or require subtraction of the PEP to determine the arterial PWTT.

Figure 8:
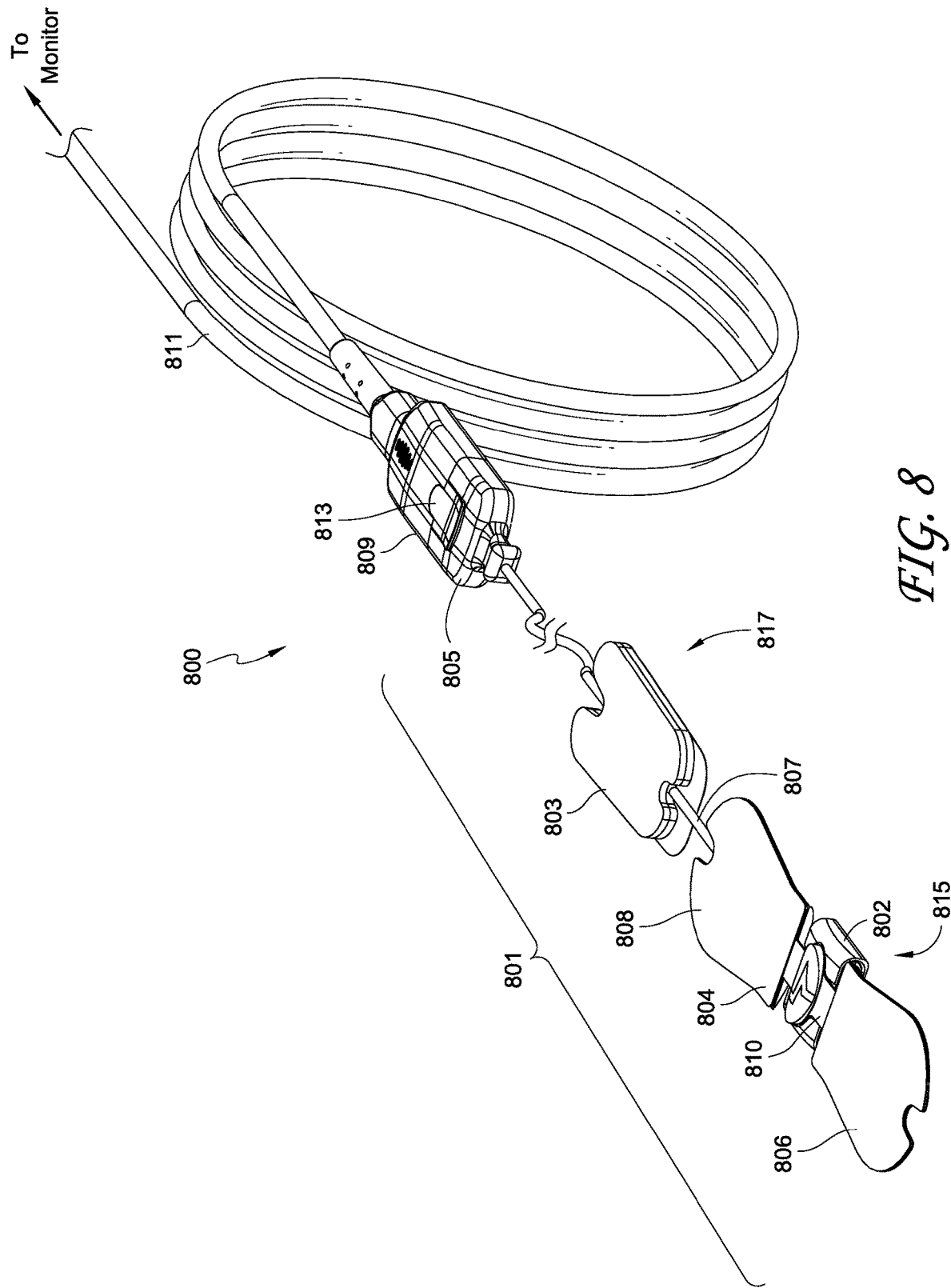
FIG. 8 illustrates an example acoustic sensor that can be used in the various systems described herein.

FIG. 8 illustrates an example acoustic sensor system 800 that can be used in any of the blood pressure monitoring systems described herein, such as the systems 100 and 300. FIG. 8 is a top perspective of a sensor system 800 including an acoustic sensor assembly 801 suitable for use as any acoustic sensor described herein and a monitor cable 811. The sensor assembly 801 can include an acoustic sensor 815, a cable assembly 817, and a connector 805. The sensor 815, in one embodiment, can include a sensor subassembly 802 and an attachment subassembly 804. The cable assembly 817 of one embodiment can include a cable 807 and a patient anchor 803. The various components can be connected to one another via the sensor cable 807. The sensor connector subassembly 805 can be removably attached to a monitor connector 809, which can be connected to parameter calculator or other physiological monitor (not shown) via the monitor cable 811. In one embodiment, the sensor assembly 801 can communicate with the physiological monitor wirelessly.

In an embodiment, the sensor assembly 801 can include a sensing element, such as, for example, a piezoelectric device or other acoustic sensing device. The sensing element can generate a voltage that is responsive to vibrations generated by the patient, and the sensor can include circuitry to transmit the voltage generated by the sensing element to a processor for processing. In an embodiment, the acoustic sensor assembly 801 can include circuitry for detecting and transmitting information related to biological sounds to a physiological monitor. These biological sounds may include heart, breathing, and/or digestive system sounds, in addition to many other physiological phenomena. The acoustic sensor 815 in certain embodiments can be a biological sound sensor, such as the sensors described herein. In some embodiments, the biological sound sensor is one of the sensors such as those described in the U.S. patent application Ser. No. 12/044,883, filed Mar. 7, 2008, entitled "Systems and Methods for Determining a Physiological Condition Using an Acoustic Monitor," which is incorporated in its entirety by reference herein. In other embodiments, the acoustic sensor 815 can include a biological sound sensor such as those described in U.S. Pat. No. 8,661,161, which is incorporated by reference herein. Other embodiments include other suitable acoustic sensors.

The attachment sub-assembly 804 can include a first elongate portion 806 and a second elongate portion 808. The first elongate portion 806 and the second elongate portion 808 can include patient adhesive (e.g., in some embodiments, tape, glue, a suction device, etc.) attached to an elongate member 810. The adhesive on the elongate portions 806, 508 can be used to secure the sensor subassembly 802 to a patient's skin. The elongate member 810 can beneficially bias the sensor subassembly 802 in tension against the patient's skin and reduce stress on the connection between the patient adhesive and the skin. A removable backing can be provided with the patient adhesive to protect the adhesive surface prior to affixing to a patient's skin.

The sensor cable 807 can be electrically coupled to the sensor subassembly 802 via a printed circuit board ("PCB") (not shown) in the sensor subassembly 802. Through this contact, signals can be communicated from the sensor subassembly to the physiological monitor via the sensor cable 807 and the cable 811.

In various embodiments, not all of the components illustrated in FIG. 8 are included in the sensor system 800. For example, in various embodiments, one or more of the patient anchor 803 and the attachment subassembly 804 are not included. In one embodiment, for example, a bandage or tape is used instead of the attachment subassembly 804 to attach the sensor subassembly 602 to a measurement site. Moreover, such bandages or tapes may be a variety of different shapes including generally elongate, circular and oval, for example.

Figure 9A:
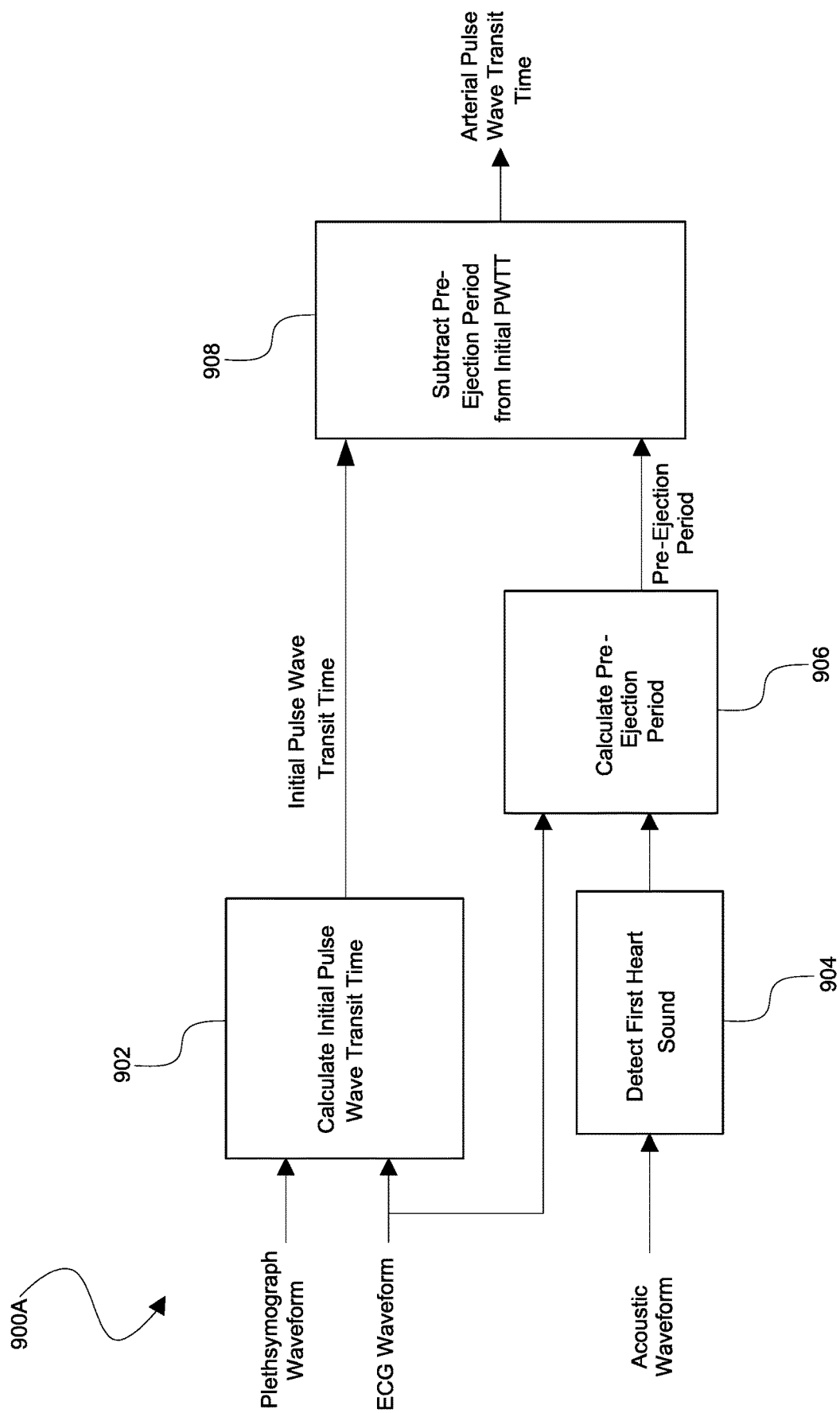
FIGS. 9A through 9F illustrate embodiments of calculating arterial PWTT.
Figure 9B:
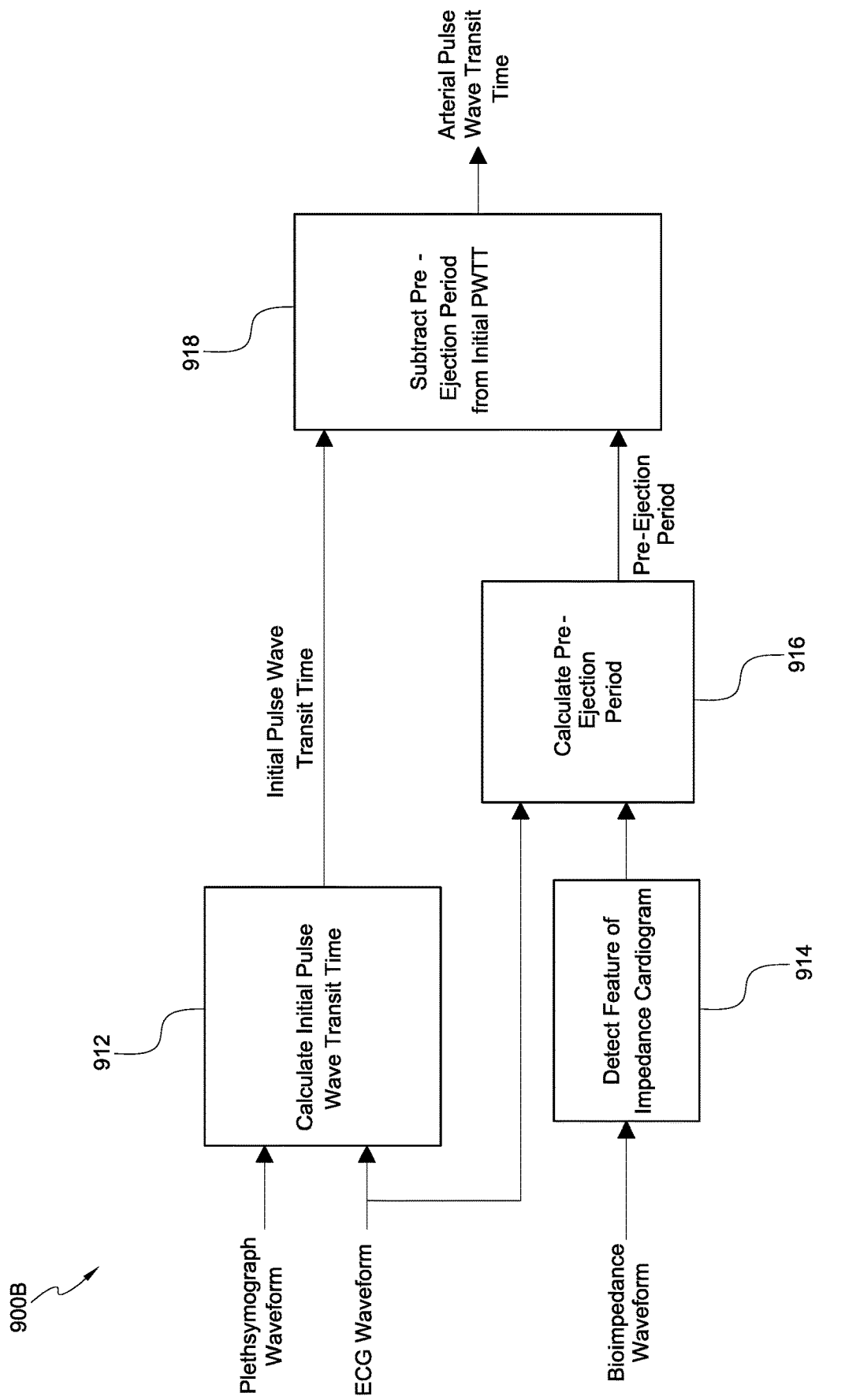
Figure 9C:
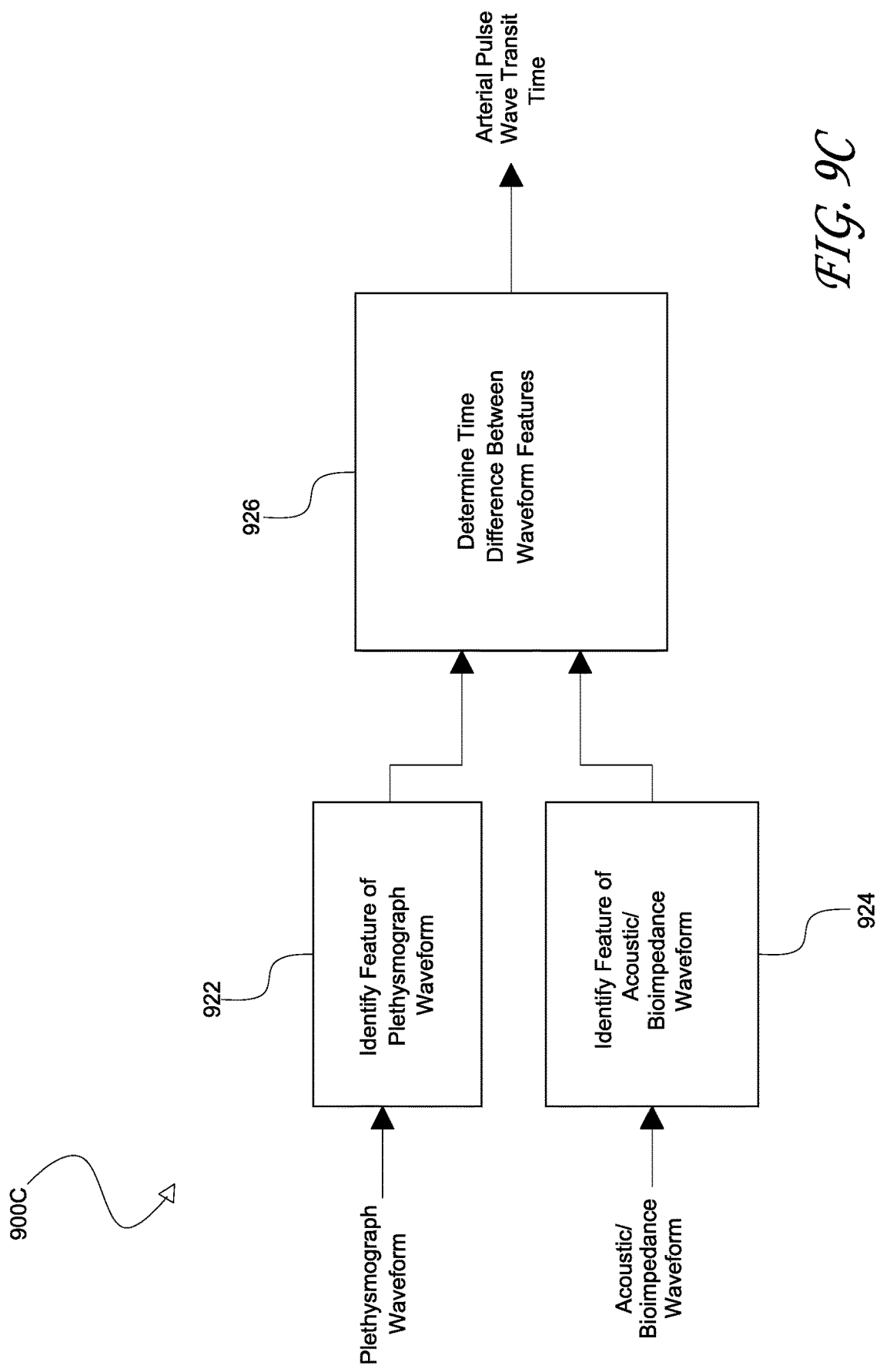

FIGS. 9A, 9B, and 9C illustrate embodiments of processes 900A, 900B, and 900C for calculating PWTT values compensated for PEP. The processes 900A, 900B, 900C can be implemented as part of any of the blood pressure monitoring systems described herein, such as the blood pressure monitoring systems 100, 300, 500A, and 500B. More particularly, the process 900A illustrates an embodiment of obtaining compensated PWTT using information obtained from an acoustic sensor. The process 900B illustrates an embodiment of PWTT calculation using bioimpedance sensors. The process 900C illustrates an embodiment of calculating PWTT without using an ECG sensor.

Referring specifically to FIG. 9A, plethysmograph, ECG, and acoustic waveforms are received by the process 900A. At block 902, an initial PWTT is calculated from the plethysmograph and ECG waveforms. This initial PWTT is determined in one embodiment by determining a time difference between features of the ECG and plethysmograph waveforms. Features on these waveforms can be determined using signal processing techniques including, but not limited to, taking derivatives of the waveforms, detecting peaks and troughs of the waveform, comparing the waveforms to models and/or thresholds, and the like. For example, an R-wave peak on an ECG waveform can be determined by detecting a point at which the ECG signal is above a (potentially adaptive) threshold and the derivative of the ECG signal is zero. As another example, a foot point on a plethysmograph waveform can be identified by the point at which the derivative of the plethysmograph waveform is zero in a time window defined after an R-wave peak. Such signal processing can be performed dynamically in real time. Alternatively or additionally, such signal processing can be performed during post processing of data.

As described above, this initial PWTT can include the arterial PWTT as well as the PEP. Thus, to obtain the arterial PWTT, further blocks of the process 900A can determine PEP so as to compensate the initial PWTT for the PEP. At block 904, a first heart sound is detected from the acoustic waveform. The PEP is then calculated at block 906 by determining a time difference between a feature of the ECG waveform and a feature of the first heart sound. The feature used on the ECG waveform to calculate the PEP 906 can be the same feature used to calculate the initial PWTT at block 902. Alternatively, different ECG features can be used to calculate PEP and the initial PWTT. At block 908, the PEP is subtracted from the initial PWTT to produce an arterial PWTT value. This arterial PWTT value can be used in determining if an automatic occlusive cuff should take a blood pressure measurement from a patient (see FIG. 10).

Advantageously, in certain embodiments, the process 900A can be performed continuously or substantially continuously so as to monitor a patient's arterial PWTT over time. The process 900A can therefore dynamically determine a patient's changing PEP over time and can compensate initial PWTT values according to this changing PEP. The process 900A can therefore, in certain embodiments, calculate more accurate PWTT than currently-available devices.

It should further be noted that the process 900A shown can also be more accurate than processes that calculate the arterial PWTT without using an ECG waveform. Because of its prominent R-wave peak, the ECG waveform can be a more reliable triggering point than cardiac ejection signals such as heart sounds or bioimpedance signals. Accordingly, the ECG signal can be used to identify relevant cardiac ejection signal. For example, the subsequent cardiac ejection signal after an ECG signal may be the next cardiac ejection signal of interest.

Another advantage of using the ECG as a triggering signal for calculating PWTT is related to the occasional ambiguity of the cardiac ejection signal. In some cases, it may be difficult or impossible to distinguish a cardiac ejection signal from noise. In such cases, the parameter calculator 110 or 310 can use the previous PEP value as the current PEP value and calculate arterial PWTT as the difference between the ECG-to-arterial pulse signal and the previous PEP value. As PEP values may change infrequently, this substitution may be accurate.

Further, because the occurrence and/or location of the cardiac ejection signal can be ambiguous, it can be beneficial to more aggressively average the PEP measurements over time to compensate for this ambiguity. For example, a relatively slower averaging filter, which may include a longer time window of data points, may be applied to the PEP values. In contrast, the overall PWTT values may change more rapidly (see, e.g., FIG. 11), and it may be beneficial to apply a relatively faster averaging filter having a relatively shorter time window to these values.

FIG. 9B illustrates another embodiment of a process 900B that uses bioimpedance information to calculate arterial PWTT. The process 900B is substantially similar to the process 900A, except that the process 900B analyzes a bioimpedance waveform instead of an acoustic waveform.

Like the process 900A, the process 900B receives a plethysmograph waveform and an ECG waveform. At block 912, an initial PWTT is calculated from these waveforms in the manner described above with respect to FIG. 9A. At block 914, the bioimpedance waveform (or impedance cardiogram) is analyzed to detect a feature, such as a foot point, a peak change in impedance, an inflection point, or the like. At block 916, the PEP is calculated as a time difference between a feature of the ECG waveform and the feature on the bioimpedance waveform. For example, the point of maximum impedance change can be compared with a feature of the ECG waveform to determine the PEP. At block 918, the calculated PEP value is subtracted form the initial PWTT to determine the arterial PWTT. This arterial PWTT value can be used in determining if an automatic occlusive cuff should take a blood pressure measurement from a patient (see FIG. 10).

Like the process 900A, the process 900B can be performed continuously or substantially continuously so as to monitor a patient's arterial PWTT over time. The process 900B can therefore dynamically determine a patient's changing PEP over time and can compensate initial PWTT values according to this changing PEP. The process 900B can therefore, in certain embodiments, calculate more accurate PWTT than currently-available devices.

FIG. 9C illustrates another embodiment of a process 900C for calculating PWTT. However, the process 900C can advantageously calculate PWTT using an optical and acoustic signal or an optical and bioimpedance signal, without using an ECG signal. Thus, the process 900C uses fewer sensors to calculate arterial PWTT.

The process 900C receives a plethysmograph and acoustic waveform, or a plethysmograph and bioimpedance waveform. At block 922, a feature of the plethysmograph waveform is identified. At block 924, a feature of the acoustic or bioimpedance waveform is identified. Cardiac ejection can precede the arrival of the resulting pulse at an extremity. Thus, a feature from the plethysmograph waveform obtained at the extremity can be identified when it occurs at a later time than the identified feature from the acoustic or bioimpedance waveform.

At block 926, a time difference between the identified waveform features is determined. This time is the arterial PWTT. This arterial PWTT value can be used in determining if an automatic occlusive cuff should take a blood pressure measurement from a patient (see FIG. 10).

Like the processes 900A and 900B, the process 900C can be performed continuously or substantially continuously so as to monitor a patient's arterial PWTT over time. The process 900C can therefore dynamically determine a patient's changing PEP over time and can compensate initial PWTT values according to this changing PEP. The process 900C can therefore, in certain embodiments, calculate more accurate PWTT than currently-available devices.

The process 900C can be modified in one embodiment to receive an ECG signal input to assist with identifying the feature of the plethysmograph waveform at block 922. It can be difficult to properly identify features from the plethysmograph waveform due to the double-peak nature of the waveform, as well as due to noise. An ECG signal, on the other hand, can have clearly-identifiable landmarks, including the R wave peak, among others. An ECG signal can therefore be used as a gating function to determine which feature of the plethysmograph waveform should be considered and/or which feature of the acoustic or bioimpedance waveform should be considered. In one embodiment, the first peak, foot point, or other feature in the plethysmograph occurring after a feature identified from the ECG signal can be identified as the relevant plethysmograph feature. Similarly, the first foot peak, or other feature of the acoustic or bioimpedance waveform occurring after a feature identified from the ECG signal can be identified as the relevant cardiac ejection signal feature. The ECG signal can therefore resolve ambiguities in the plethysmograph waveform, thereby improving noise immunity and/or noise reduction. Similarly, the ECG signal can also be used as a reliable identifier of a cardiac ejection signal, thereby improving the accuracy of the arterial PWTT calculation.

Figure 9D:
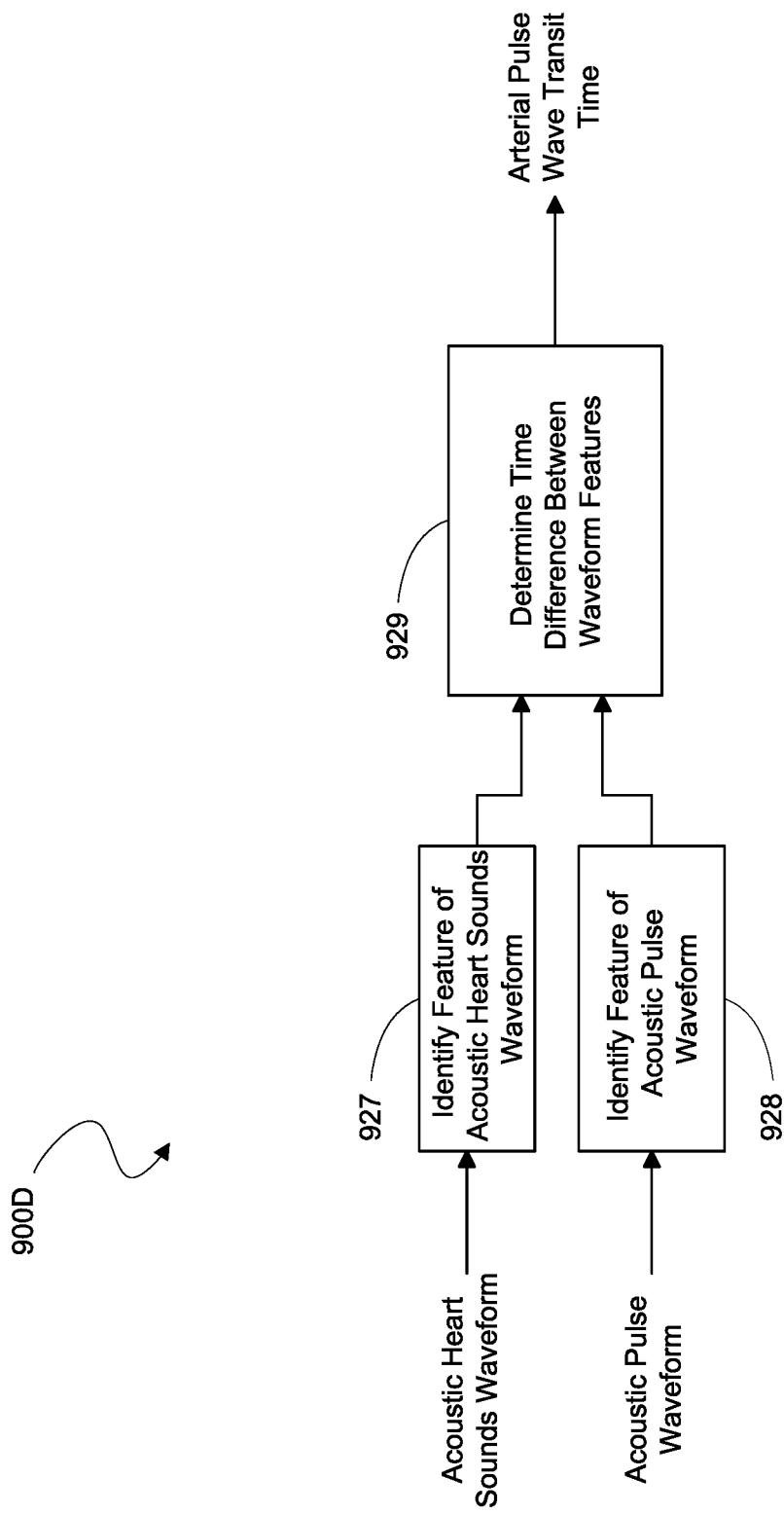
Figure 9E:
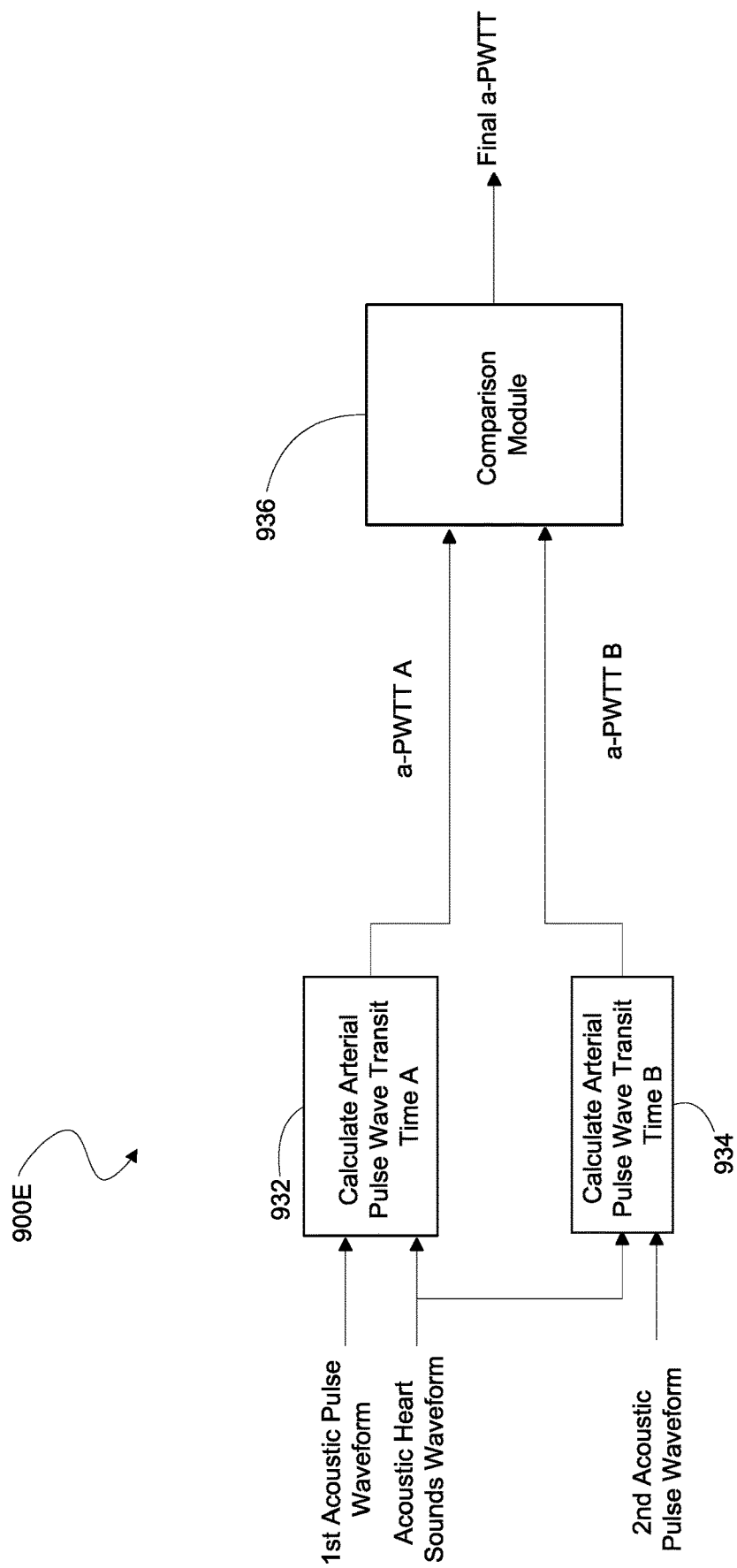
Figure 9F:
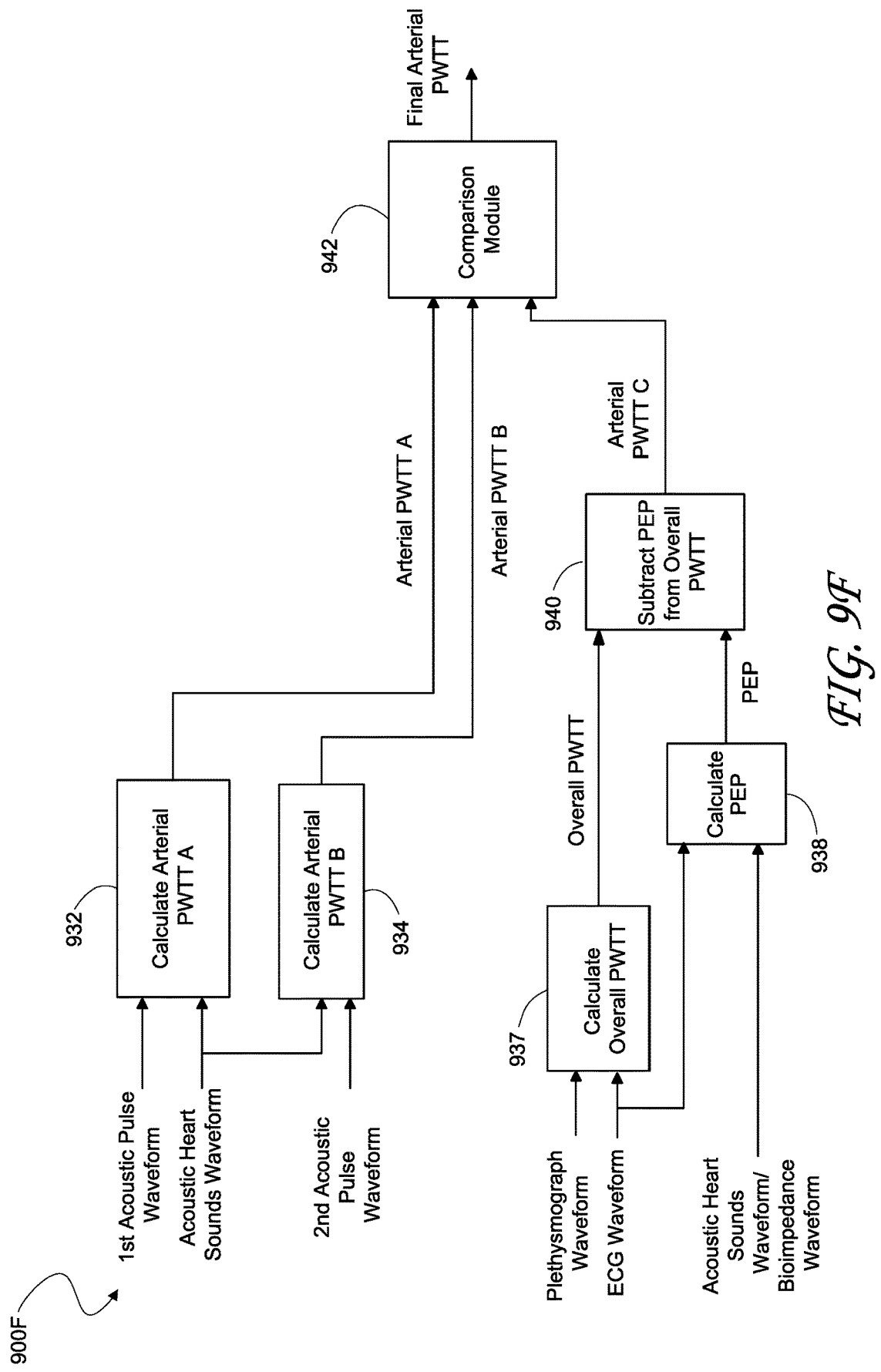

FIGS. 9D-9F illustrate additional embodiments of processes 900D, 900E, 900F for calculating arterial PWTT values, refining calculated arterial PWTT values, and/or determining confidence of arterial PWTT values. In some implementations, arterial PWTT values are determined from acoustic waveforms of signals from only two acoustic sensors, as described in connection with FIG. 9D. In other implementations, arterial PWTT values are determined using waveforms of signals from three or more acoustic sensors (as described in connection with FIG. 9E) or from one or more non-acoustic sensors, in addition to the two acoustic sensors (as described in connection with FIG. 9F). Each of the depicted blocks or modules of the processes 900 can be implemented by hardware and/or software modules.

With reference to FIG. 9D, the process 900D can advantageously calculate arterial PWTT using two acoustic signals, without using an ECG signal. Thus, the process 900D uses two mechanical signals rather than one electrical signal and one mechanical signal, thereby improving stability and accuracy of the arterial PWTT calculations. The use of the two acoustic signals also removes the necessity to subtract out the PEP component of the overall PWTT and instead reflects the arterial PWTT alone.

The process 900D receives an acoustic heart sounds waveform and an acoustic pulse waveform. The acoustic pulse waveform can be, for example, an acoustic wrist pulse waveform or an acoustic carotid pulse waveform, as described above; however, the acoustic pulse waveform can be received from an acoustic sensor positioned at other locations as well. At block 927, a feature of the acoustic heart sounds waveform is identified. At block 928, a feature of the acoustic pulse waveform is identified. The feature of the acoustic heart sounds waveform can correspond to the time of cardiac ejection, which precedes the time of arrival of the resulting pulse at a location of the acoustic sensor from which the acoustic pulse waveform is generated.

Features on these waveforms can be determined using signal processing techniques including, but not limited to, taking derivatives of the waveforms, detecting peaks and troughs of the waveform, comparing the waveforms to models and/or thresholds, determining the centroid of a feature of the waveform, taking an envelope of a portion of the waveform and identifying a feature of the envelope, combinations of the same, and the like. For example, a foot point on an acoustic waveform can be identified by the point at which the derivative of the acoustic waveform is zero in a time window defined after an electrical trigger (e.g., as identified by an ECG sensor). As another example, a centroid or "middle" of a pulse, burst or waveof an acoustic waveform can be determined. In some embodiments, the centroid can be determined by constructing an amplitude envelope of the pulse, sound burst, or pressure wave and then performing a normalized weighting of each time point according to the envelope amplitude, with the highest energy point of the envelope being the centroid time of the pulse or sound (e.g., heart sound). The centroid determination can be performed in the time domain or frequency domain. In some embodiments, the centroid determination includes sampling and/or filtering of the pulse, sound burst, or pressure wave. Such signal processing can be performed dynamically, in real time. Alternatively or additionally, such signal processing can be performed during post processing of data.

At block 929, a time difference between the identified waveform features is determined. This time can be considered to be the arterial PWTT in one embodiment. This arterial PWTT value can be used in determining if an automatic occlusive cuff should take a blood pressure measurement from a patient (see FIG. 8). The process 900D can be performed continuously or substantially continuously so as to monitor a patient's arterial PWTT over time. Alternatively, the process 900D can be performed as a spot-check upon occurrence of predetermined conditions or at predetermined time intervals.

The process 900D can be modified in one embodiment to receive an ECG signal input to assist with identifying the feature of the acoustic heart sounds waveform at block 927. It can be difficult to properly identify features from acoustic waveforms due to noise or other characteristics. An ECG signal, on the other hand, can have clearly-identifiable landmarks, including the R wave peak, among others. An ECG signal can therefore be used as a gating function to determine which heart sound should be considered. In one embodiment, the first heart sound of the acoustic heart sounds waveform occurring after a feature identified from the ECG signal can be identified as the relevant acoustic heart sounds feature. The ECG signal can therefore resolve ambiguities in the acoustic waveforms, thereby improving noise immunity and/or noise reduction. In some embodiments, the ECG signal can be used to identify the transition from electrical to mechanical behavior. The time delay between the ECG signal and the first heart sound (e.g., S1 sound) detected by the acoustic heart sounds sensor can provide an indication of the health of the heart or other potential pathological conditions that may warrant medical attention. However, the ECG signal input is not used or needed in other embodiments.

FIGS. 9E and 9F illustrate embodiments of processes 900E, 900C for determining PWTT values, refining calculated PWTT values, and/or determining confidence of PWTT values. More particularly, the process 900E illustrates an embodiment of a process for calculating, refining, or assessing PWTT values using information obtained from multiple acoustic sensors, one of which is an acoustic heart sounds sensor. The process 900C illustrates an embodiment of a system for arterial PWTT calculation, refinement, or assessment using acoustic sensors in conjunction with additional sensors, such as ECG sensors, optical sensors, and/or bioimpedance sensors. The processes 900E, 900C can be implemented as part of the parameter calculation system 100 or the blood pressure monitoring system 300. Each of the depicted blocks or modules of the processes 900 can be implemented by hardware and/or software modules.

Referring specifically to FIG. 9E, the process 900E receives three acoustic waveforms. These three acoustic waveforms can include an acoustic heart sounds waveform and two acoustic pulse waveforms (a first pulse waveform and a second pulse waveform). For example, the acoustic pulse waveforms can include a wrist pulse waveform and a carotid pulse waveform. The acoustic heart sounds waveform and a first pulse waveform (e.g., wrist pulse waveform) can be received by PWTT determination block 932 and the acoustic heart sounds waveform and a second pulse waveform can be received by PWTT determination block 934. The PWTT determination block 932 can calculate a first arterial PWTT (a-PWTT A) value from the acoustic heart sounds waveform and the first acoustic pulse waveform. The PWTT determination block 934 can calculate a second arterial PWTT (a-PWTT B) value from the acoustic heart sounds waveform and the second acoustic pulse waveform. These initial arterial PWTT measurements are determined in one embodiment by determining a time difference between features of the acoustic heart sounds waveform and the acoustic pulse waveform (as described in connection with FIG. 9A).

In some implementations, the initial arterial PWTT values (a-PWTT A and a-PWTT B) can be provided to a comparison module 936. The comparison module 906 can analyze the two initial arterial PWTT values to generate a final arterial PWTT output value. In some implementations, the comparison module 936 can compare the two initial arterial PWTT values to determine a difference between the two values. The comparison module 936 can derive a confidence value from the calculated difference. In other implementations, the comparison module 936 can average or otherwise combine the two initial arterial PWTT values to output a refined final arterial PWTT output value. In some embodiments, the two initial arterial PWTT values are weighted. In yet other implementations, the comparison module 936 can select one of the two initial arterial PWTT values to output as the final arterial PWTT output value. The comparison module 936 can make this selection based on confidence values, based on comparison to historical data or thresholds, based on patient-specific factors, and/or the like.

In some embodiments, the second pulse acoustic waveform can simply be used to provide another reference or gating point in identifying a feature of the first pulse acoustic waveform. In other embodiments, the second pulse acoustic waveform can be used to identify other patient characteristics (e.g., patient breaths, respiratory rate, respiratory pause, or other respiratory conditions, as discussed above).

FIG. 9F illustrates an embodiment of a process 900C that uses information obtained from one or more non-acoustic sensors in addition to one or more acoustic sensors to calculate, refine, or assess arterial PWTT measurements.

Like the process 900E, the process 900E can calculate two arterial PWTT values (a-PWTT A and a-PWTT B) at PWTT determination blocks 932 and 934, respectively. The process 900C can also receive an ECG signal input, a plethysmograph signal input, and/or a bioimpedance signal input in addition to the acoustic signal inputs. An overall PWTT value (including arterial PWTT and PEP components) can be calculated at PWTT determination block 937 by determining a time difference between a feature of a plethysmograph waveform and a feature of an ECG waveform. Further blocks of the process 900C can determine PEP so as to compensate the overall PWTT for the PEP. The PEP is calculated at block 938 by determining a time difference between a feature of the ECG waveform and a feature of the acoustic heart sounds waveform or a bioimpedance waveform in the manner described above. The feature used on the ECG waveform to calculate the PEP 938 can be the same feature used to calculate the overall PWTT at block 936. Alternatively, different ECG features can be used to calculate PEP and the overall PWTT. At block 940, the PEP is subtracted from the initial PWTT to produce a third arterial PWTT value (a-PWTT C).

In other embodiments, the third arterial PWTT value can be derived from a time difference between a feature of an acoustic waveform or a bioimpedance waveform and a pleth waveform such that PEP need not be calculated, as described above.

Similar to the process 900E, the three arterial PWTT values can be received by the comparison module 936 and analyzed to output a final arterial PWTT value. In some implementations, the comparison module 936 can compare the three initial arterial PWTT values to determine differences between any two of the three values. The comparison module 936 can derive a confidence value from the calculated differences. In other implementations, the comparison module 936 can average or otherwise combine the three initial arterial PWTT values to output a refined final arterial PWTT output value. In some embodiments, the three initial arterial PWTT values are weighted. In yet other implementations, the comparison module 936 can select one of the three initial arterial PWTT values to output as the final arterial PWTT output value. The comparison module 936 can make this selection based on confidence values, based on comparison to historical data or thresholds, based on patient-specific factors, and/or the like.

In other embodiments, arterial PWTT values can be calculated using one or more non-acoustic sensors in combination with one or more acoustic sensors. For example, arterial PWTT values can be calculated from time differences between a feature of a bioimpedance waveform (e.g., generated from signals received from two bioimpedance sensors) and a feature of an acoustic waveform (e.g., received from an acoustic pulse sensor positioned over or proximate a wrist, leg or carotid artery).

Figure 10:
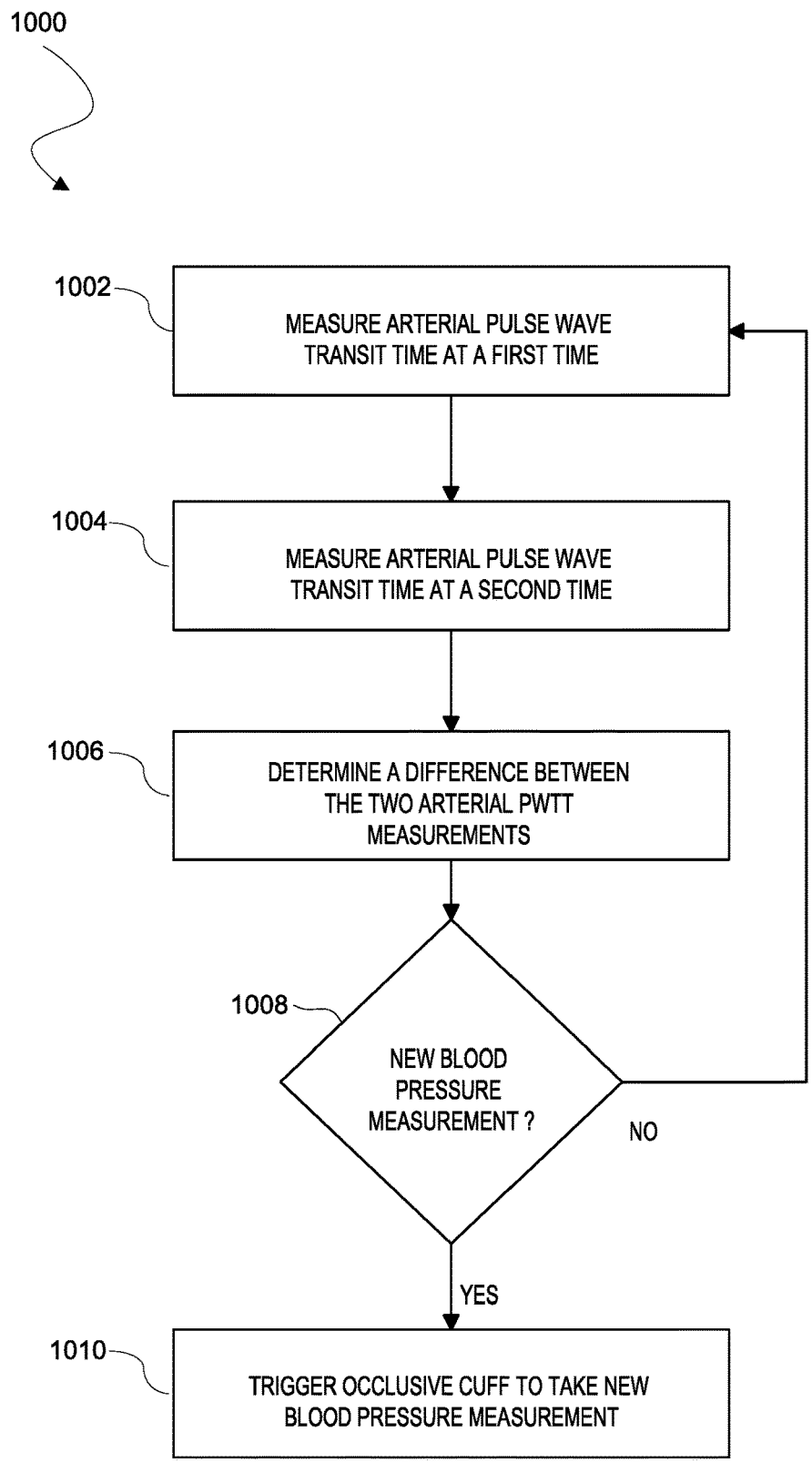
FIG. 10 illustrates an embodiment of a process for triggering an occlusive blood pressure measurement.

FIG. 10 illustrates an embodiment of a process 1000 for determining whether to trigger an alternative blood pressure measurement. This process 1000 can be implemented by any of the systems 100, 300, described above. Advantageously, in certain embodiments, the process 1000 can determine, based at least partly on non-invasive PWTT measurements, whether to trigger an automatic occlusive cuff. As a result, continuous or substantially continuous monitoring of a user's blood pressure can occur, allowing the frequency of occlusive cuff measurements to potentially be reduced.

At block 1002, a first arterial PWTT measurement is determined at a first point in time. The arterial PWTT can be determined using any of the techniques above, such as by calculating PEP and by compensating an overall PWTT value with the PEP. Similarly, a second arterial PWTT measurement is taken at a second point in time at block 1004. These arterial PWTT measurements can be taken from successive heart beats in one embodiment. In another embodiment, the first and second arterial PWTT values each represent arterial PWTT values averaged over multiple heartbeats.

At block 1006, a difference between the two arterial PWTT measurements is determined. It is then determined at decision block 1008 whether a new blood pressure measurement is required. In certain embodiments, this decision can be made by determining whether the difference between the two measurements is greater than a threshold. A difference greater than a threshold can be indicative of a change in a patient's blood pressure. Therefore, if the difference is greater than the threshold, an occlusive cuff is triggered to take a new blood pressure measurement at block 1010. If the difference is not greater than the threshold, then the process 1000 loops back to block 1002. Effectively, the process 1000 therefore can trigger occlusive cuff measurements when the threshold is exceeded and can continue monitoring arterial PWTT measurements otherwise.

In certain embodiments, the process 1000 analyzes changes in arterial PWTT measurements using an absolute difference technique or a moving difference technique. With the absolute difference technique, the process 1000 measures the PWTT at a first fixed time. Subsequent arterial PWTT measurements (e.g., the second measurement at block 1004) are compared to the initial arterial PWTT at the first fixed time to determine whether the difference between these measurements exceeds a threshold. With the moving difference technique, the first and second arterial PWTT measurements are compared for successive points in time. The first arterial PWTT measurement is therefore not taken at a fixed time but instead changes over time. Thus, the moving difference technique can approximate a derivative of the arterial PWTT measurements. The moving difference can be compared to a threshold at block 1008. An advantage of using the moving difference technique is that it can potentially ignore drifts in arterial PWTT measurements due to calibration changes or other errors.

Thus, in certain embodiments, the process 1000 can refrain from triggering an occlusive cuff until the non-invasive measurement differs enough to trigger such a measurement. Advantageously, in certain embodiments, the process 1000 can therefore allow a user to postpone the discomfort and potential physiological damage associated with occlusive blood pressure measurements, while the non-invasive measurement (e.g., arterial PWTT) is within a certain tolerance.

Although the PWTT measurements have been described herein as being used to trigger an occlusive cuff, in certain embodiments the PWTT measurements can also or instead be used to derive an estimate of blood pressure. A calibration function or curve can be determined that maps PWTT measurements to blood pressure values. The slope and intercept of the calibration curve can be determined experimentally.

PWTT Noise Compensation

Figure 11:
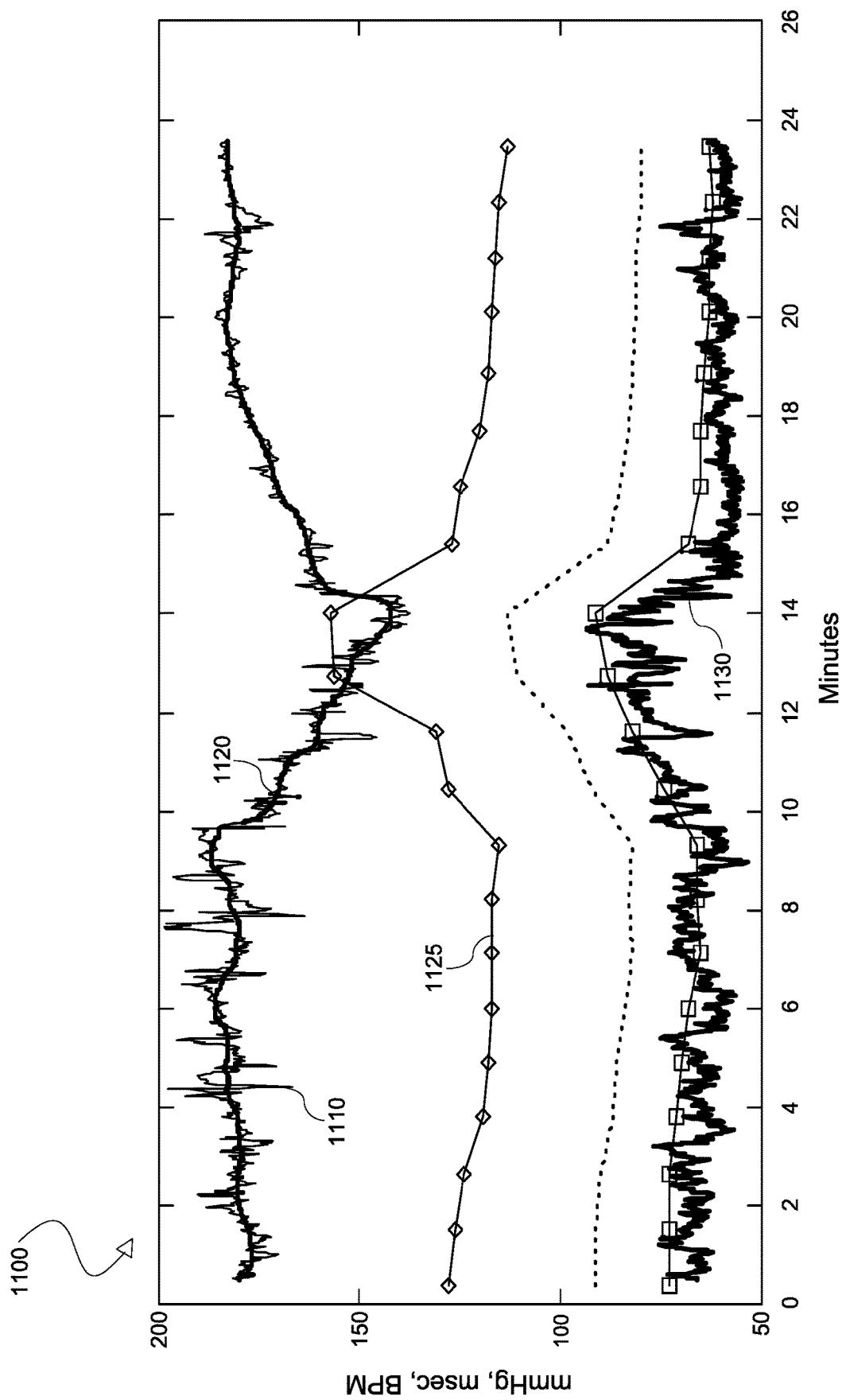
FIG. 11 illustrates plots of PWTT and heart rate waveforms.
Figure 12:
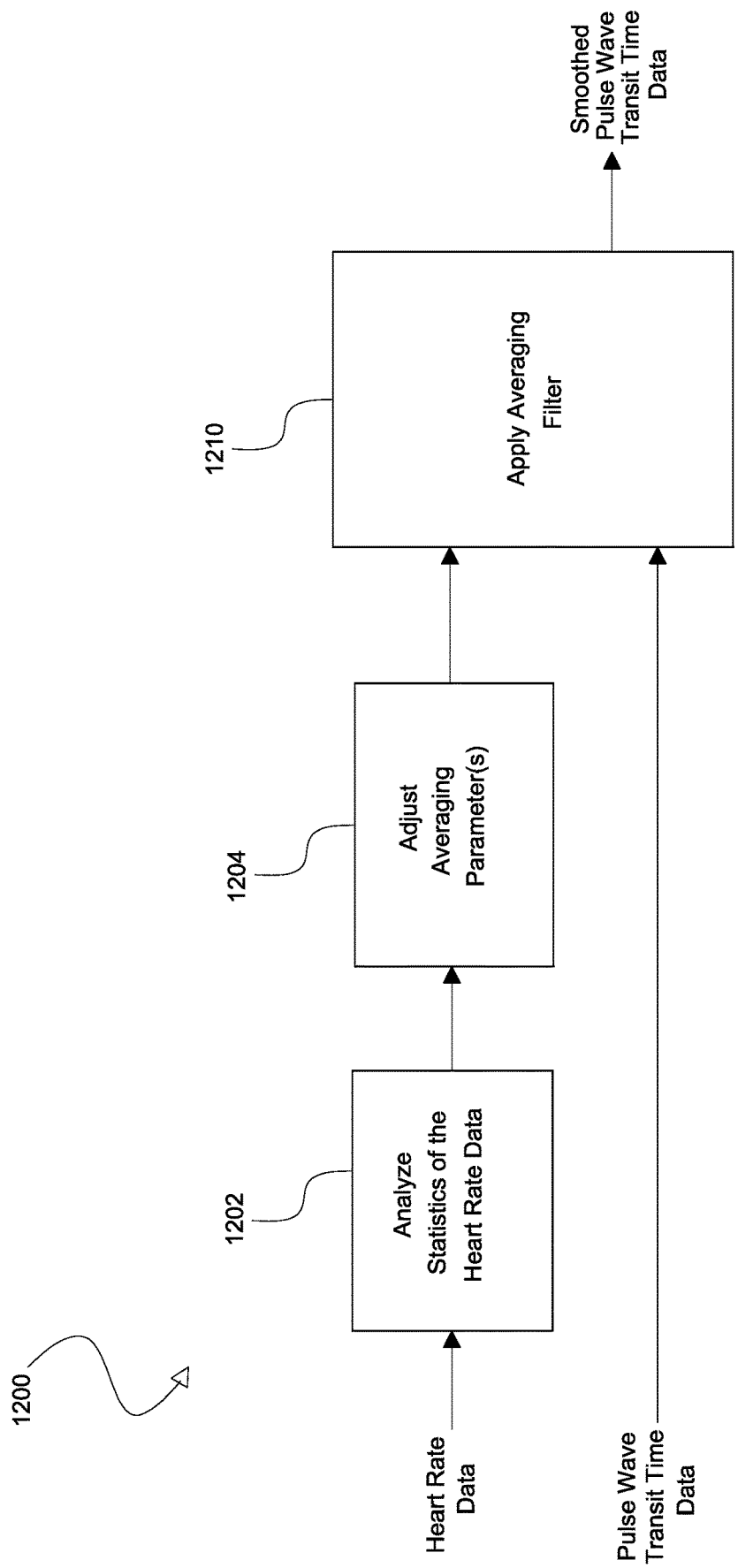
FIG. 12 illustrates an embodiment of a dynamic PWTT averaging system.

As described above, in addition to compensating PWTT for PEP, the parameter calculation system 100 can also compensate PWTT data for noise. FIGS. 11 and 12 illustrate embodiments for compensating PWTT data for noise. By compensating PWTT data for noise, more accurate PWTT measurements can be obtained. The features described with respect to FIGS. 11 and 12 can be used in combination with any of the features described herein.

FIG. 11 depicts an example plot 1100 that illustrates noise in a set of arterial PWTT data. In the example plot 1100, PWTT values taken over time are represented as a PWTT waveform 1110. Variability in the PWTT waveform 1110 reflects noise in the PWTT waveform 1110. Noisy PWTT data can lead to lower quality PWTT measurements, resulting in too frequent or too infrequent triggering of a blood pressure cuff. In certain circumstances, noisy PWTT can even lead to missing a clinically significant change in blood pressure.

One technique to reduce the effects of noise in the PWTT data is to average the PWTT data over time. A time-averaged PWTT waveform 1120 is shown in FIG. 11. The average can be calculated from PWTT data points taken over a certain time period. PWTT data points can be averaged by applying a smoothing filter, such as a low pass filter. Determining a number of PWTT data points and/or an averaging time to include in an average can involve tradeoffs. A longer averaging time can reduce the presence of noise in the PWTT data. However, a longer averaging time can also reduce the benefits of using PWTT as an indicator of blood pressure to trigger an occlusive cuff. For example, a long averaging time can cause rapidly-changing features on a waveform to be missed. In contrast, a shorter averaging time using fewer data PWTT data points may not sufficiently filter out noise.

In certain embodiments, averaging can be improved by dynamically adjusting the averaging time according to the amount of noise present in the PWTT data. If a higher level of noise is present, a longer averaging time can be selected. Conversely, if less noise is present, a shorter averaging time can be used. However, it can be difficult to differentiate noise from signal in the PWTT data. Thus, determining the level of the noise in the PWTT data and therefore the amount of averaging to perform can be nontrivial.

To select an appropriate averaging time, in one embodiment a signal correlated with the PWTT data can be analyzed. Heart rate is such a correlated signal, and respiratory rate is another. An example heart rate signal is shown plotted over time as a waveform 1130 in FIG. 11. The variability of the heart rate waveform 1130 corresponds to the variability of the PWTT data 1110, indicating that the heart rate and PWTT can be correlated. The heart rate waveform 1130 (or respiratory rate) can therefore be analyzed to determine the amount of noise present in the PWTT data to thereby select an averaging time for the PWTT data. Likewise, in some applications, such as where accurate heart rate measurements are desired, it can be useful to analyze the PWTT data to determine an averaging time for the heart rate data. Dynamic signal averaging is described in greater detail below with respect to FIG. 10.

Another possible use of the heart rate (or respiratory rate) data is to use the heart rate (or respiratory rate) as a noise reference in an adaptive filter. For example, the system 100 (or any other system described herein) can adaptively filter or adaptively cancel noise in the PWTT data using the heart rate as a noise reference. Any of a variety of adaptive algorithms can be used by the parameter calculation system 100. For instance, the adaptive algorithm can implement one or more of the following: a least mean squares algorithm (LMS), a least squares algorithm, a recursive least squares (RLS) algorithm, a Kalman filter, a joint process estimator, an adaptive joint process estimator, a least-squares lattice joint process estimator, a least-squares lattice predictor, a correlation canceller, optimized or frequency domain implementations of any of the above, any other linear predictor, combinations of the same, and the like. In still other embodiments, the PWTT data can be both adaptively filtered and averaged using a dynamically-adjusted averaging filter.

Further, as can be seen in FIG. 11, the PWTT data in the waveforms 1110 or 1120 can be correlated with a systolic blood pressure data 1125 over time. As shown, the relationship between the PWTT data and the systolic blood pressure data 1125 can be inverse or approximately inverse.

FIG. 12 illustrates an embodiment of a signal averaging process 1200. The signal averaging process 1200 can be implemented by any of the systems 120, 300, 500A, or 500B described above. Advantageously, in certain embodiments, the process 1200 uses heart rate data to dynamically adjust the averaging time of an averaging filter applied to the PWTT data.

At block 1202, statistics of the heart rate data are analyzed to determine a measure of the noise in the heart rate data. A variety of statistics of the heart rate data can be calculated at block 1202, including variance, standard deviation, and entropy, combinations of the same, and the like. For example, the standard deviation can be calculated from the heart rate data to measure the degree of dispersion or variability in the heart rate data. A higher standard deviation can reflect greater variability in the heart rate data, which can in turn reflect more noise in the heart rate data. Conversely, a lower standard deviation can reflect lower noise in the heart rate data. More generally, any measure of variation or change in the heart rate data can be calculated at block 1202.

At block 1204, one or more averaging parameters of an averaging filter can be adjusted based on the statistical calculation. In one embodiment, an averaging parameter such as averaging time is adjusted. For example, if the standard deviation of the heart rate data is relatively high, reflecting more noise, a relatively long averaging time can be selected. On the other hand, if the standard deviation is relatively lower, reflecting less noise, a relatively shorter averaging time can be selected. More generally, the one or more averaging parameters can include any parameter of the averaging filter that can be tuned. The averaging parameters can therefore include the order of the averaging filter, the number of points averaged (e.g., for a simple moving average filter), the time constant of the filter (e.g., for a low pass averaging filter), and an array of coefficients for more complex averaging filters (such as any of the adaptive filters described above with respect to FIG. 9).

At block 1210, the averaging filter with the selected averaging time is applied to the PWTT data. Averaging can include computing a mean, median, and/or mode. In some embodiments, a weighted average of PWTT measurements can be applied. For example, the averaging filter can place a greater weight on more recent PWTT data and/or data with a corresponding statistic that indicates lower variability. For signals with relatively lower variability in the heart rate data, the averaging filter may not be applied to the PWTT input at all. Further, in other embodiments, the statistics of the PWTT signal can be evaluated to determine the amount of noise and therefore averaging time, rather than evaluating the statistics of the heart rate signal.

Phase Impact Reduction

Figure 13:
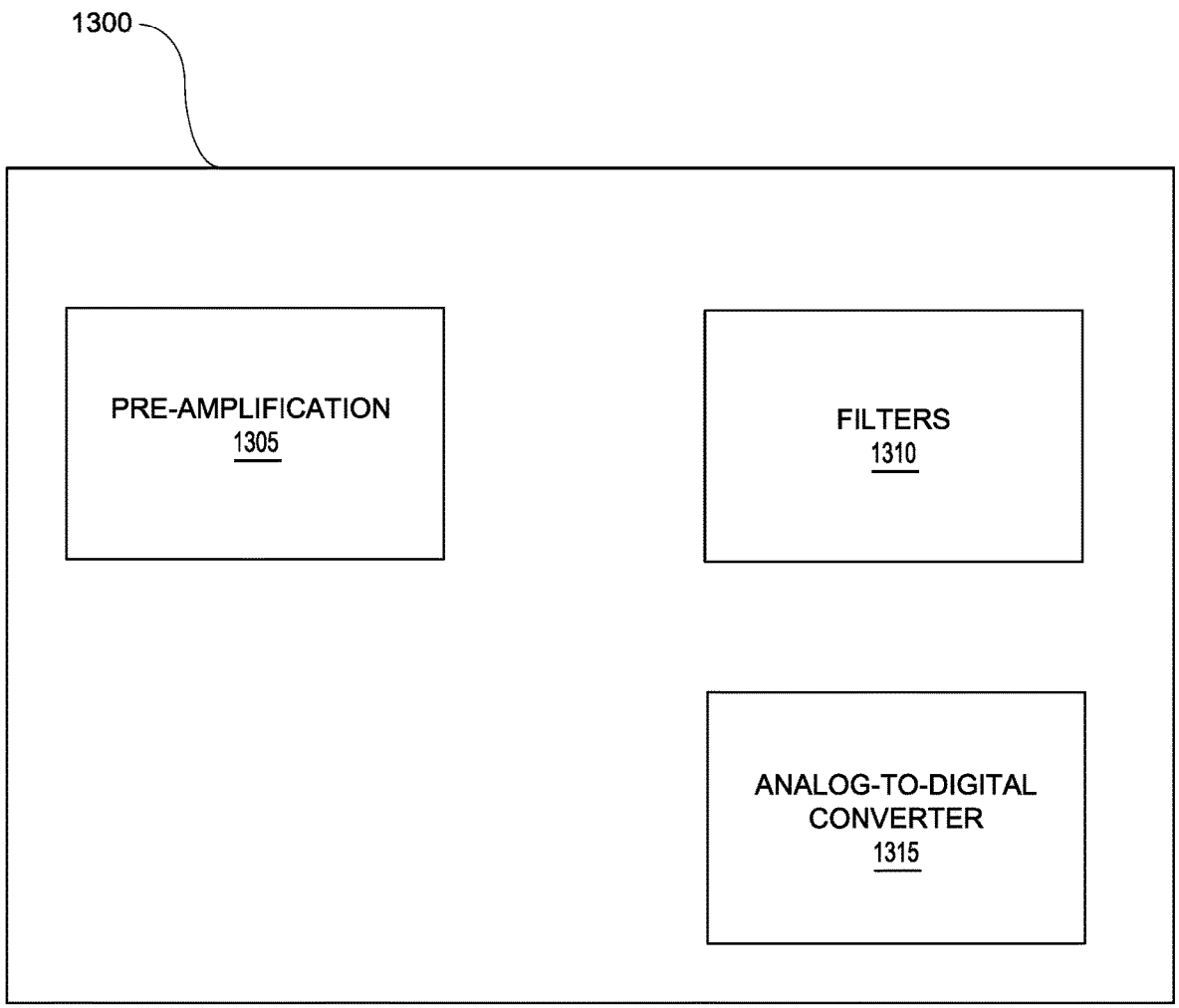
FIG. 13 illustrates an embodiment of front end circuitry that can be used in the parameter calculation systems described herein to reduce phase impact on the calculations of PWTT.

In some embodiments, the PWTT measurements and calculations described herein are determined in terms of time. Accordingly, phase delay or phase noise can be introduced between successive filters of the parameter calculation system or blood pressure monitoring system. FIG. 13 illustrates an embodiment of front end circuitry 1300 that can be configured to condition analog electrical signals output by the acoustic sensors for processing. In some embodiments, the front end circuitry 1300 can reduce the phase impact introduced into the system. The front end circuitry 1300 can include a pre-amplification module 1305, one or more filters 1310, and an analog-to-digital converter (ADC) 1315.

The pre-amplification module 1305 can receive and amplify the voltage signal from the acoustic sensors, such as by a predetermined gain. In some implementations, the pre-amplification module 1305 introduces a high input impedance to drop the high pass filtering effect of the piezoelectric acoustic sensors. In some implementations, the pre-amplification module 1305 includes circuitry to convert an AC signal output from the acoustic sensor to a DC signal. In some implementations, the one or more filters 1310 include one or more low pass filters to allow the low frequency heart and pulse acoustic signals detected by the acoustic sensors while attenuating high frequency signals, such as high frequency noise. The one or more filters 1310 may include other types of filters, such as high pass or bandpass filters, instead of or in addition to, the one or more low pass filters. In some implementations, the one or more filters 1310 can be adjusted to reduce the phase distortion by changing the location of the zeros and/or poles of the one or more filters 1310.

In some implementations, the cutoff frequency of the acoustic sensors (which can be represented as capacitors in terms of frequency response analysis) can effectively be changed to a much lower frequency than an acoustic sensor used for respiration detection (e.g., to 0.01 Hz or 0.1 Hz). According to some embodiments, the acoustic sensors can have a cutoff frequency that is inversely dependent on the capacitance of the sensor and the input resistance of the amplifier or other circuit that receives the signal. The acoustic sensors may be modified to achieve a much lower cutoff frequency. For example, the low frequency response can be extended by changing the piezoelectric characteristics of the acoustic sensor (e.g., making the capacitance of the piezoelectric material itself larger, such as by the composition, size, thickness, etc. of the piezoelectric material), by making the input resistance higher, and/or by placing a large (as compared to the piezoelectric capacitance) capacitor in shunt with the acoustic sensor. In some embodiments, rather than lowering the cutoff frequency of the acoustic sensor itself, a compensatory filter can be inserted in the signal path. In one embodiment, the cutoff frequency is allowed to be significantly higher than the frequency band of interest, such that the acoustic sensor is effectively responsive to the derivative of the signal. Thus, the compensatory filter can be an integrator, which recreates the original acoustic signal. In some embodiments, it may be neither necessary nor desirable to extend the low frequency response of the acoustic sensors. The output from the filters 1310 can be amplified into a higher voltage signal and then converted to a digital signal by the ADC converter 1315. In some embodiments, using a single ADC converter 1315 to convert each signal, or multiple of the signals, including acoustic, electrical, and/or optical, can also reduce phase distortion between the signals. Further, oversampling in the ADC 1315 can also reduce phase distortion between the signals. The digital signal can then pass to a digital signal processor for processing in preparation for display on a monitor or screen.

Patient Calibration

Figure 14A:
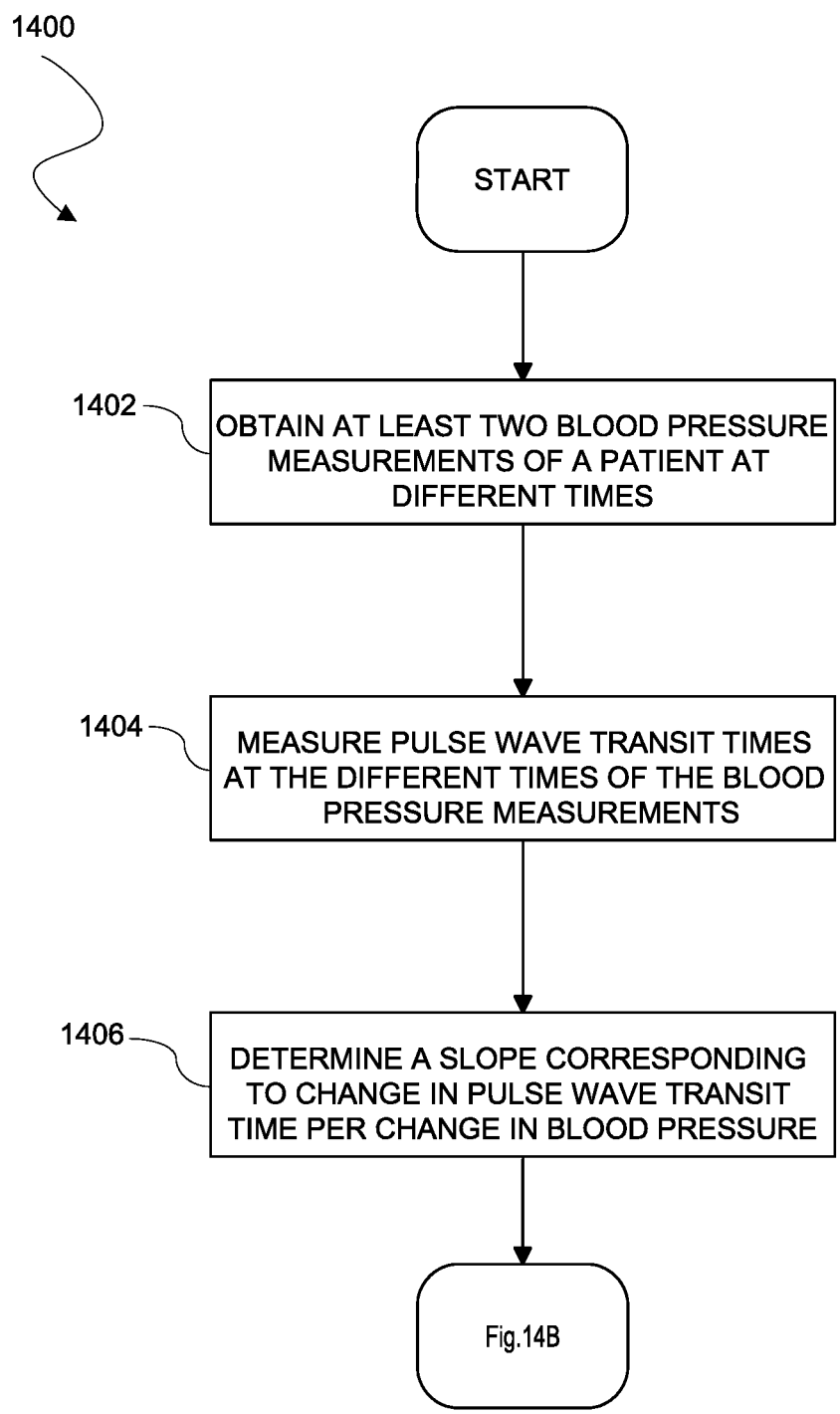
FIGS. 14A and 14B illustrate an embodiment of a process for calibrating PWTT measurements based on an individualized patient calibration factor.
Figure 14B:
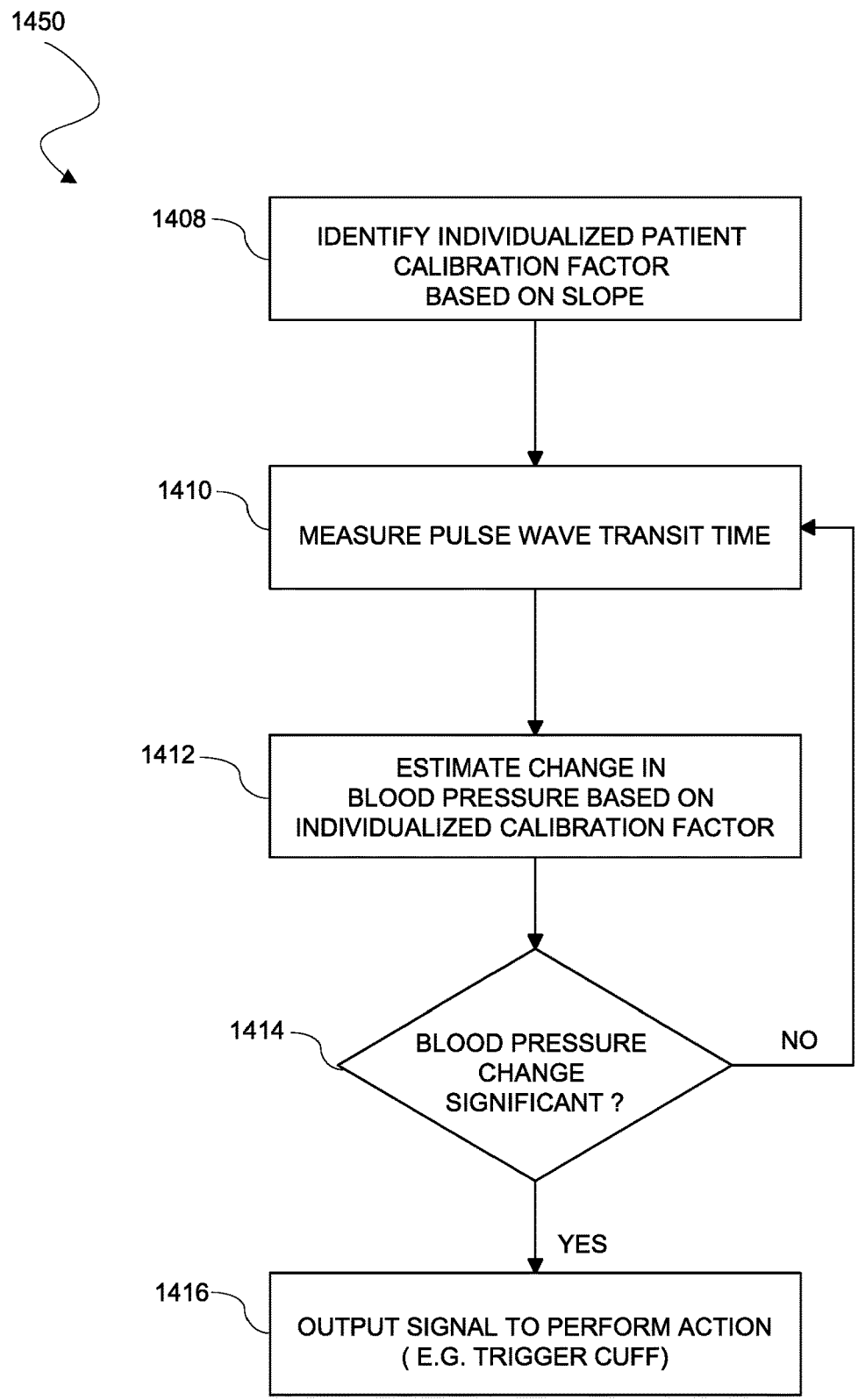

FIGS. 14A and 14B illustrate an embodiment of a process 1400 for calibrating pulse wave transit time measurements based on a personalized patient calibration factor. Pulse wave transit time measurements can vary depending on changes in blood pressure. The variance can be defined by a slope measurement, which can be the change in pulse wave transit time per the change in pressure (e.g., change in number of milliseconds per change in number of millimeters of mercury (mmHg)). The variance, or slope, of the calibration curve can differ greatly from patient to patient. For example, the slope can vary by a factor of between 2:1 to 4:1 or greater between patients. This variance can be due to a variety of physiological factors, such as hemodynamic factors of capillary flow or perfusion. The slope may also vary based on the introduction of drugs (including even blood pressure regulation drugs), patient comorbidity, gender, age, or other factors. Accordingly, it can be advantageous to determine the slope of the PWTT/blood pressure calibration curve for the individual patient and use the determined slope to interpret subsequent PWTT measurements.

The individualized patient calibration process 1400 can reduce the effect of slope variability between patients by uniquely and individually calibrating the PWTT measurements for the individual patient, thereby reducing the inaccuracy of blood pressure measurement frequency or false alarms based on PWTT measurements. The individualized patient calibration process 1400 therefore advantageously provides a mechanism for more efficient interpretation of PWTT measurements for individual patients by compensating for the variability of slope. Alternatively, in one embodiment, a patient monitor (such as any of those described herein) can calculate a baseline PWTT variability offset that is applied to the calculation of PWTT for multiple patients. This baseline adjustment may, but need not, be calibrated to individual patients or segments of patients (e.g., segments for drug users, segments based on gender, age, or comorbidity).

The term PWTT measurements as used herein with respect to FIGS. 14A and 14B can refer to overall PWTT (including PEP and a-PWTT components) or arterial PWTT. The individualized patient calibration process 1400 can be implemented by the blood pressure monitoring systems and/or parameter calculation systems described herein (e.g., systems 140 and 300).

The calibration process 1400 begins at block 1402, wherein at least two blood pressure measurements of a patient are obtained at different times. The blood pressure measurements can include just systolic blood pressure measurements, just diastolic blood pressure measurements, and/or combinations of the systolic and diastolic blood pressure measurements (for example, mean or median blood pressure measurements).

In some implementations, blood pressure measurements can be taken at two different elevations of known hydrostatic pressure at two different times. For example, a first blood pressure measurement can be taken when the patient is lying down on a bed or table with the arm at the patient's side and a second blood pressure measurement can be taken with the arm raised up at least approximately perpendicularly to the patient's body. The blood pressure measurements can be normalized to account for changes in pressure due to the change in elevation. The changes in pressure due to the change in elevation can be determined based on a measured or known distance between the locations of the measurements and calculated or known hydrostatic pressure and/or based on actual hydrostatic pressure measurements. The distance and/or pressure measurements can be obtained by any of a variety of sensors or transducers. In some embodiments, a wrist cuff is used to obtain the blood pressure measurements (which, in some embodiments, reduces the effects of the arterial-to-capillary time delays addressed above). Other methods can be used to obtain blood pressure measurements over time in accordance with yet other implementations.

At block 1404, pulse wave transit times are measured to correspond with the blood pressure measurements. Although block 1404 is illustrated as occurring after block 1402, the pulse wave transit times can be measured simultaneously or substantially simultaneously (e.g., within a few seconds or within a few milliseconds) with the blood pressure measurements. Accordingly, the pulse wave transit times can be mapped to their corresponding blood pressure measurements. The blood pressure measurements and pulse wave transit time measurements can be stored in memory (at least temporarily). In some embodiments, the memory can include a predetermined capacity of measurements and the oldest measurements can be replaced by new measurements when capacity has been reached. The stored measurements can be used to generate a calibration curve defined by a plot of the pulse wave transit times on one axis (e.g., vertical axis) and the corresponding blood pressure measurements on the other axis (e.g., horizontal axis).

At block 1406, an individual patient's slope corresponding to the change in pulse wave transit time per change in blood pressure (e.g., slope of the calibration curve) is determined from the blood pressure and PWTT measurements obtained at block 1402 and block 1404. A patient's PWTT ms/mmHg slope can be determined from two or more blood pressure measurements and two or more corresponding PWTT measurements. In accordance with some embodiments, the slope is inferred over time from a plurality of frequent blood pressure and corresponding PWTT measurements. The slope determination can then be refined over time through less frequent natural blood pressure and corresponding PWTT measurements.

Based on the determined slope of the patient, a personalized, or individualized, patient calibration factor can be identified at block 1408 and used to interpret subsequent pulse wave transit time measurements of the patient with reduced concern for patient variability.

At block 1410, a pulse wave transit time is measured (for example, an arterial pulse wave transit time can be measured as described herein). At block 1412, the process 1400 estimates a change in the patient's blood pressure based on the measured pulse wave transit time. The measured pulse wave transit time has been calibrated using the individualized patient calibration factor, thereby reducing patient variability.

At decision block 1414, the process 1400 determines whether the estimated blood pressure change satisfies a condition that warrants performance of an action (e.g., whether the estimated blood pressure change is significant enough to perform an action). The condition can be, for example, a blood pressure change that exceeds a threshold blood pressure change value, cuff triggering value, a patient alarm triggering value, and/or the like. The condition can be patient-specific based on patient-specific factors or generic to all patients. If the condition is satisfied, the process 1400 proceeds to block 1416, wherein an appropriate action is performed based on the satisfied condition. For example, if an estimated blood pressure change exceeds a threshold change, a blood pressure cuff measurement can be triggered to determine and/or confirm the accuracy of the estimated blood pressure change. In some embodiments, the new blood pressure measurement can be added to a running tally to refine the individualized patient calibration factor.

As another example, if an estimated blood pressure change exceeds an alarm condition, a patient alarm can be triggered so that the patient can receive immediate medical attention. In some embodiments, the alarm is triggered only if confidence in the estimated blood pressure change is above a predetermined level. In some embodiments, a blood pressure measurement is obtained to confirm the accuracy of the estimated blood pressure change prior to triggering an alarm.

In some implementations, the determination of whether the blood pressure change is significant enough to warrant an action at block 1408 includes a multivariate determination based on other factors in addition to pulse wave transit time (e.g., heart rate). For example, if heart rate and pulse wave transit time are changing, it is more likely that the blood pressure is changing in a manner such that an action is recommended to be performed.

In some situations, the patient's calibration curve slope can change due to changes in patient conditions (e.g., changes in hemodynamic state, introduction of drugs, etc.). Accordingly, in some implementations, the slope is tracked over time to determine whether a recalibration process may be recommended. Other inputs or physiological parameters, such as heart rate, can be analyzed in determining whether recalibration of the personalized patient calibration factor should be performed as well.

In other implementations, a slope of a patient's blood pressure over time can be determined instead of, or in addition to, the PWTT/blood pressure calibration curve slope and used to identify a personalized patient calibration factor, which can in turn be used to interpret pulse wave transit time measurements.

Terminology

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. For example, the vehicle management system 110 or 210 can be implemented by one or more computer systems or by a computer system including one or more processors.

The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and/or write information to, the storage medium. The storage medium can be external to or remote from the processor. For example, the storage medium may be a storage device accessible by the processor over a network. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method of monitoring blood pressure of a user, the method comprising:
    under control of a hardware processor,
        detecting a cardiac ejection signal from a first sensor coupled with a user, the cardiac ejection signal indicative of when blood is ejected from the user's heart;
        receiving an arterial pulse signal from a second sensor non-invasively coupled with the user's wrist, the arterial pulse signal indicative of when a blood pressure pulse arrives at the user's wrist;
        calculating a pulse wave transit time (PWTT) measurement by determining a time between a feature of the cardiac ejection signal and a feature of the arterial pulse signal;
        dynamically adjusting an averaging filter to apply to a plurality of PWTT measurements to adaptively filter noise in the plurality of PWTT measurements and average the plurality of PWTT measurements, wherein properties of the averaging filter depend on characteristics of heart rate data;
        applying the dynamically adjusted averaging filter to the plurality of PWTT measurements;
        deriving a blood pressure measurement based at least in part on the averaged plurality of PWTT measurements; and
        outputting the blood pressure measurement.

2. The method of claim 1, further comprising smoothing one or both of the cardiac ejection signal and the arterial pulse signal prior to calculating the PWTT.

3. The method of claim 1, wherein the first sensor is configured to be coupled with the user's body at a location other than the chest.

4. The method of claim 1, wherein the first sensor is configured to be coupled with the user's chest.

5. The method of claim 1, further comprising calculating the PWTT by at least determining a time difference from a centroid of a first heart sound in the cardiac ejection signal to the feature of the arterial pulse signal.

6. The method of claim 1, using an electrocardiogram (ECG) signal as a gating function to detect a feature to consider in the cardiac ejection signal.

7. The method of claim 1, wherein at least one of the first sensor and the second sensor is not an acoustic sensor.

8. A system for monitoring blood pressure of a user, the system comprising:
    a first sensor that couples with a user, the first sensor configured to output a cardiac ejection signal from the user, the cardiac ejection signal indicative of when blood is ejected from the user's heart;
    a second sensor coupled with the user, the second sensor configured to output an arterial pulse signal at the user's wrist, the arterial pulse signal indicative of when a blood pressure pulse arrives at the user's wrist;

a hardware processor configured to:
- calculate a pulse wave transit time (PWTT) by determining a time between a feature of the cardiac ejection signal and a feature of the arterial pulse signal;
- dynamically adjust an averaging filter to apply to a plurality of PWTT measurements to adaptively filter noise in the plurality of PWTT measurements and average the plurality of PWTT measurements, wherein properties of the averaging filter depend on characteristics of heart rate data;
- apply the dynamically adjusted averaging filter to the plurality of PWTT measurements;
- derive a blood pressure measurement based at least in part on the averaged and filtered plurality of PWTT measurements; and
- a display that outputs the blood pressure measurement.

9. The system of claim 8, wherein the hardware processor is further configured to smooth one or both of the cardiac ejection signal and the arterial pulse signal prior to calculating the PWTT.

10. The system of claim 8, wherein the first sensor includes and an acoustic sensor and is configured to be coupled with the user's body at a location other than the chest.

11. The system of claim 8, wherein the first sensor is configured to be coupled with the user's chest.

12. The system of claim 8, wherein the hardware processor is further configured to calculate the PWTT by at least determining a time difference from a centroid of a first heart sound in the cardiac ejection signal to the feature of the arterial pulse signal.

13. The system of claim 8, wherein the hardware processor is further configured to use an electrocardiogram (ECG) signal as a gating function to detect a feature to consider in the cardiac ejection signal.

14. The system of claim 8, wherein at least one of the first sensor and the second sensor is not an acoustic sensor.

* * * * *